(12) United States Patent
Yamanaka

(10) Patent No.: US 12,383,329 B2
(45) Date of Patent: Aug. 12, 2025

(54) GRIPPING DEVICE AND TREATMENT TOOL

(71) Applicant: Olympus Corporation, Tokyo (JP)

(72) Inventor: Noriaki Yamanaka, Tokyo (JP)

(73) Assignee: Olympus Corporation, Tokyo (JP)

( * ) Notice: Subject to any disclaimer, the term of this patent is extended or adjusted under 35 U.S.C. 154(b) by 549 days.

(21) Appl. No.: 18/047,867

(22) Filed: Oct. 19, 2022

(65) Prior Publication Data

US 2023/0104511 A1 Apr. 6, 2023

Related U.S. Application Data

(63) Continuation of application No. PCT/JP2020/017391, filed on Apr. 22, 2020.

(51) Int. Cl.
*A61B 18/14* (2006.01)
*A61B 18/00* (2006.01)

(52) U.S. Cl.
CPC ...... *A61B 18/1445* (2013.01); *A61B 2018/00607* (2013.01); *A61B 2018/144* (2013.01); *A61B 2018/1455* (2013.01)

(58) Field of Classification Search
CPC ........ A61B 17/295; A61B 2018/00601; A61B 2018/00607; A61B 2018/144; A61B 18/1442; A61B 18/1445; A61B 18/1447; A61B 2018/145; A61B 2018/1452; A61B 2018/1455

See application file for complete search history.

(56) References Cited

U.S. PATENT DOCUMENTS

| | | | |
|---|---|---|---|
| 2011/0054467 A1* | 3/2011 | Mueller | A61B 18/1445 606/205 |
| 2011/0251608 A1 | 10/2011 | Timm et al. | |
| 2012/0041438 A1* | 2/2012 | Nau, Jr. | A61B 18/1445 606/45 |

(Continued)

FOREIGN PATENT DOCUMENTS

JP 2019037801 A 3/2019

OTHER PUBLICATIONS

"International Application Serial No. PCT/JP2020/017391, International Search Report dated Jun. 16, 2020", (Jun. 16, 2022), 2 pgs.

*Primary Examiner* — Linda C Dvorak
*Assistant Examiner* — Bradford C. Blaise
(74) *Attorney, Agent, or Firm* — Schwegman Lundberg & Woessner, P.A.

(57) ABSTRACT

A gripping device includes: a gripping portion including a first gripping piece including a first gripping surface, and a second gripping piece including a second gripping surface, the second gripping surface being configured to grip a living tissue; and a first wire extending from a first end to a second end of the first wire, an incision portion that is a part of the first wire between the first end and the second end being bridged between the first gripping surface and the second gripping surface, the first wire being configured such that the incision portion moves from a first position toward a distal end of the gripping portion according to pulling of at least one of the first end and the second end to incise the living tissue gripped between the first gripping surface and the second gripping surface.

12 Claims, 26 Drawing Sheets

(56) References Cited

U.S. PATENT DOCUMENTS

| | | | |
|---|---|---|---|
| 2012/0296332 A1* | 11/2012 | Chernov | A61B 17/3201 |
| | | | 606/45 |
| 2014/0214030 A1* | 7/2014 | Horlle | A61B 18/1445 |
| | | | 606/45 |
| 2015/0305803 A1 | 10/2015 | Larson et al. | |
| 2017/0086905 A1 | 3/2017 | Chernov et al. | |
| 2018/0161052 A1 | 6/2018 | Weir et al. | |
| 2021/0244465 A1* | 8/2021 | Zhao | A61B 18/1206 |

* cited by examiner

GRIPPING DEVICE AND TREATMENT TOOL

CROSS-REFERENCE TO RELATED APPLICATION

This application is a continuation of International Application No. PCT/JP2020/017391, filed on Apr. 22, 2020, the entire contents of which are incorporated herein by reference.

BACKGROUND

1. Technical Field

The present disclosure relates to a gripping device and a treatment tool.

2. Related Art

In the related art, there has been known a gripping device that incises a site (hereinafter, described as a target site) to be treated in a living tissue with an incision blade while gripping the site with a pair of gripping pieces (see, for example, JP 2019-37801 A).

In the gripping device described in JP 2019-37801 A, a wire (driving system) is connected to the incision blade. Then, the incision blade is pushed by the wire to move from a proximal end toward a distal end between the pair of gripping pieces. As a result, the target site gripped between the pair of gripping pieces is incised.

SUMMARY

In some embodiments, a gripping device includes: a gripping portion including a first gripping piece including a first gripping surface, and a second gripping piece including a second gripping surface that is relatively opened or closed with respect to the first gripping piece, the second gripping surface being configured to grip a living tissue between the second gripping surface and the first gripping surface; and a first wire extending from a first end to a second end of the first wire, an incision portion that is a part of the first wire between the first end and the second end being bridged between the first gripping surface and the second gripping surface, the first wire being configured such that the incision portion moves from a first position toward a distal end of the gripping portion according to pulling of at least one of the first end and the second end to incise the living tissue gripped between the first gripping surface and the second gripping surface.

In some embodiments, a treatment tool includes a gripping device configured to grip a living tissue, the gripping device including a gripping portion including a first gripping piece including a first gripping surface, and a second gripping piece including a second gripping surface that is relatively opened or closed with respect to the first gripping piece, the second gripping surface being configured to grip a living tissue between the second gripping surface and the first gripping surface; and a first wire extending from a first end to a second end of the first wire, an incision portion that is a part of the first wire between the first end and the second end being bridged between the first gripping surface and the second gripping surface, the first wire being configured such that the incision portion moves from a first position toward a distal end of the gripping portion according to pulling of at least one of the first end and the second end to incise the living tissue gripped between the first gripping surface and the second gripping surface.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
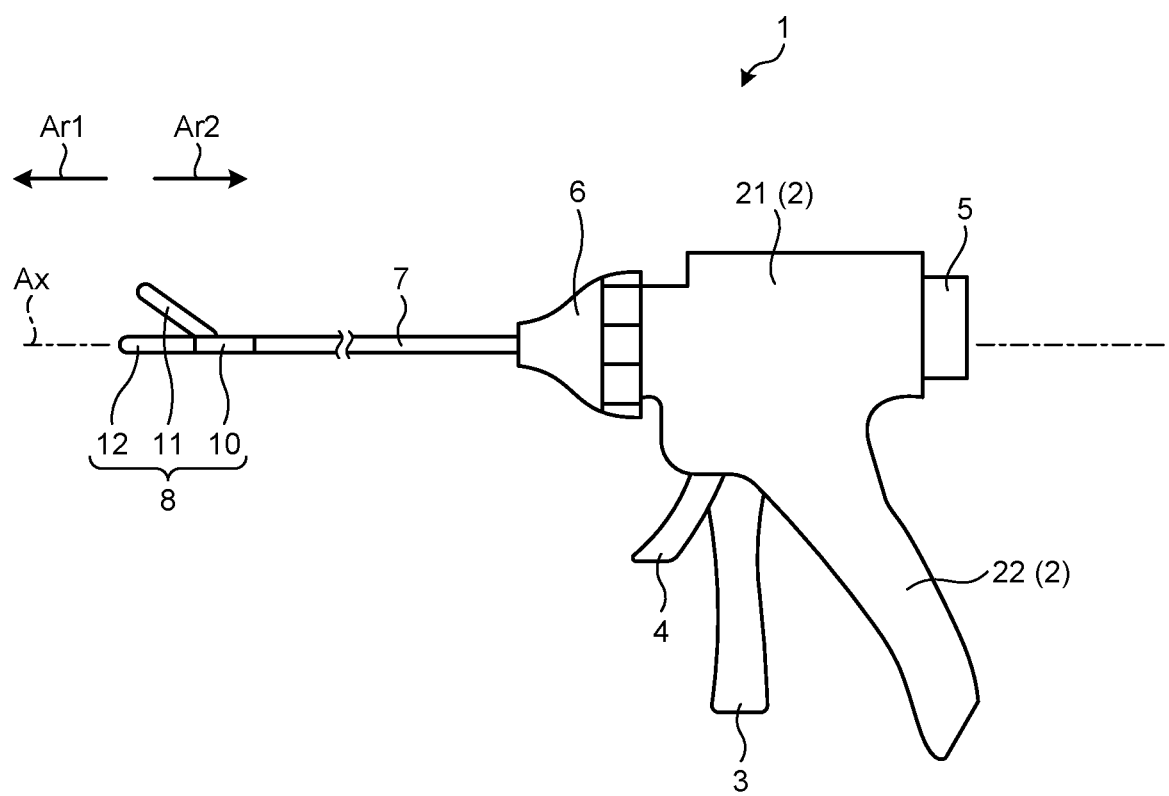
FIG. 1 is a view illustrating a configuration of a treatment tool according to a first embodiment.

Hereinafter, modes for carrying out the disclosure (embodiments) will be described with reference to the drawings.

Note that the disclosure is not limited by the embodiments described below. Furthermore, in the description of the drawings, the same portions are denoted by the same reference numerals.

First Embodiment

Configuration of Treatment Tool

FIG. 1 is a view illustrating a configuration of a treatment tool 1 according to a first embodiment.

Hereinafter, for convenience of description, one side along a central axis Ax of a shaft 7 is referred to as a distal end side Ar1, and the other side is referred to as a proximal end side Ar2 (FIG. 1).

The treatment tool 1 treats a site (hereinafter, described as a target site) to be treated in a living tissue. In the first embodiment, the treatment is incision of the target site. As illustrated in FIG. 1, the treatment tool 1 includes a housing 2, first and second movable handles 3 and 4, a bending operation portion 5, a rotary knob 6, the shaft 7, and a gripping portion 8.

The housing 2 supports the entire treatment tool 1. As illustrated in FIG. 1, the housing 2 includes a substantially cylindrical housing main body 21 coaxial with the central axis Ax, and a fixed handle 22 extending downward in FIG. 1 from the housing main body 21 and gripped by an operator.

The first movable handle 3 is pivotally supported to the housing 2 so as to be rotatable about a rotation axis (not illustrated) orthogonal to the paper surface of FIG. 1. Then, the first movable handle 3 receives an opening/closing operation by an operator. The opening/closing operation is an operation of rotating the first movable handle 3 with respect to the housing 2.

The second movable handle 4 is pivotally supported to the housing 2 so as to be rotatable about a rotation axis Rx0 (see FIG. 13) orthogonal to the paper surface of FIG. 1. The second movable handle 4 includes a columnar base portion 41 located inside the housing main body 21 and coaxial with the rotation axis Rx0, and a handle main body 42 extending from the base portion 41 to the outside of the housing 2 (see FIG. 13).

Then, the second movable handle 4 (handle main body 42) receives an incision operation by the operator. The incision operation is an operation of rotating the second movable handle 4 with respect to the housing 2 in a direction approaching the fixed handle 22 about the rotation axis Rx0. Although not specifically illustrated, the second movable handle 4 is constantly biased by a spring in a direction away from the fixed handle 22. That is, when the operator releases his/her hand from the second movable handle 4 after the incision operation is performed by the operator, the second movable handle 4 rotates with respect to the housing 2 about the rotation axis Rx0 in a direction away from the fixed handle 22 by a biasing force of the spring.

The bending operation portion 5 is pivotally supported by the housing 2 so as to be rotatable about a rotation axis (not illustrated) extending in an up-down direction in FIG. 1. Then, the bending operation portion 5 receives a bending operation by the operator. The bending operation is an operation of bending the gripping portion 8 with respect to the shaft 7, and is an operation of rotating the bending operation portion 5 with respect to the housing 2.

The rotary knob 6 has a substantially cylindrical shape extending along the central axis Ax, and is supported by the housing main body 21 so as to be rotatable about the central axis Ax in a posture coaxial with the central axis Ax. Then, the rotary knob 6 receives a rotation operation by the operator. By the rotation operation, the rotary knob 6 rotates about the central axis Ax with respect to the housing main body 21.

The shaft 7 has a substantially cylindrical shape as a whole. The gripping portion 8 is provided at an end portion on the distal end side Ar1 of the shaft 7 (FIG. 1). The end portion of the shaft 7 on the proximal end side Ar2 is inserted into the rotary knob 6, and is fixed to the inner surface of the rotary knob 6 by welding or the like. That is, the shaft 7 and the gripping portion 8 rotate about the central axis Ax together with the rotary knob 6 in response to the rotation operation of the rotary knob 6 by the operator.

A part of an opening/closing mechanism (not illustrated) that opens and closes first and second gripping pieces 11 and 12 (FIG. 1) constituting the gripping portion 8 according to the opening/closing operation to the first movable handle 3 by the operator is inserted into the shaft 7. As a part of the opening/closing mechanism, a wire or a rod can be exemplified.

Furthermore, first and second wires W1 and W2 (see FIG. 12) used to incise the target site gripped between the first and second gripping pieces 11 and 12 according to the incision operation on the second movable handle 4 by the operator are inserted into the shaft 7. A detailed configuration of the first and second wires W1 and W2 will be described later.

In the shaft 7, a part (third and fourth wires W3 and W4 (see FIG. 4)) of a bending mechanism (not illustrated) for bending the gripping portion 8 with respect to the shaft 7 in accordance with the bending operation of the bending operation portion 5 by the operator is inserted.

The gripping portion 8 is a part that treats the target site. The gripping portion 8 and the first and second wires W1 and W2 correspond to a gripping device 9 (see FIG. 11).

Hereinafter, a detailed configuration of the gripping portion 8 will be described.

Configuration of Gripping Portion

Figure 2:
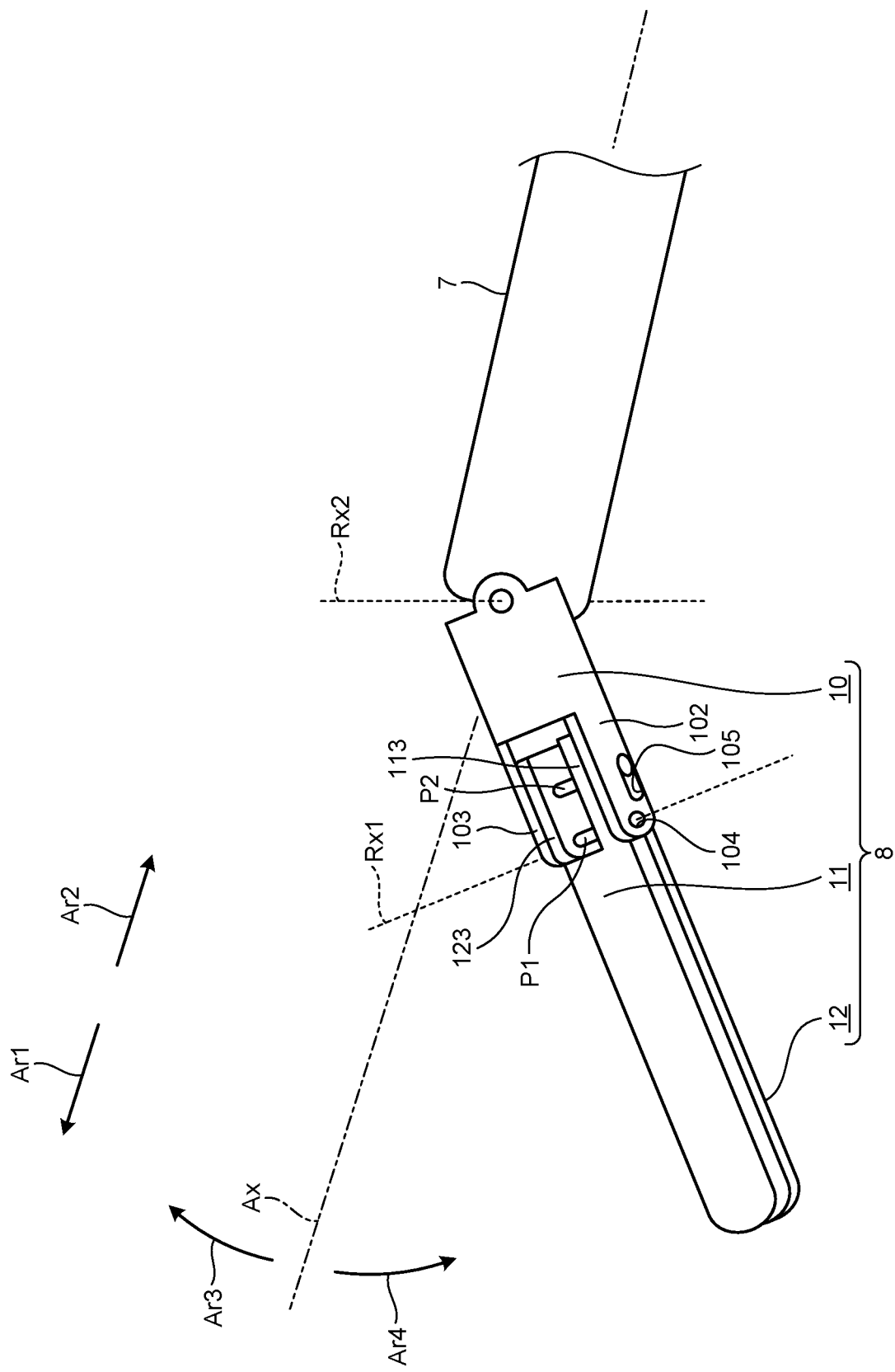
FIG. 2 is a view illustrating a configuration of a gripping portion.
Figure 3:
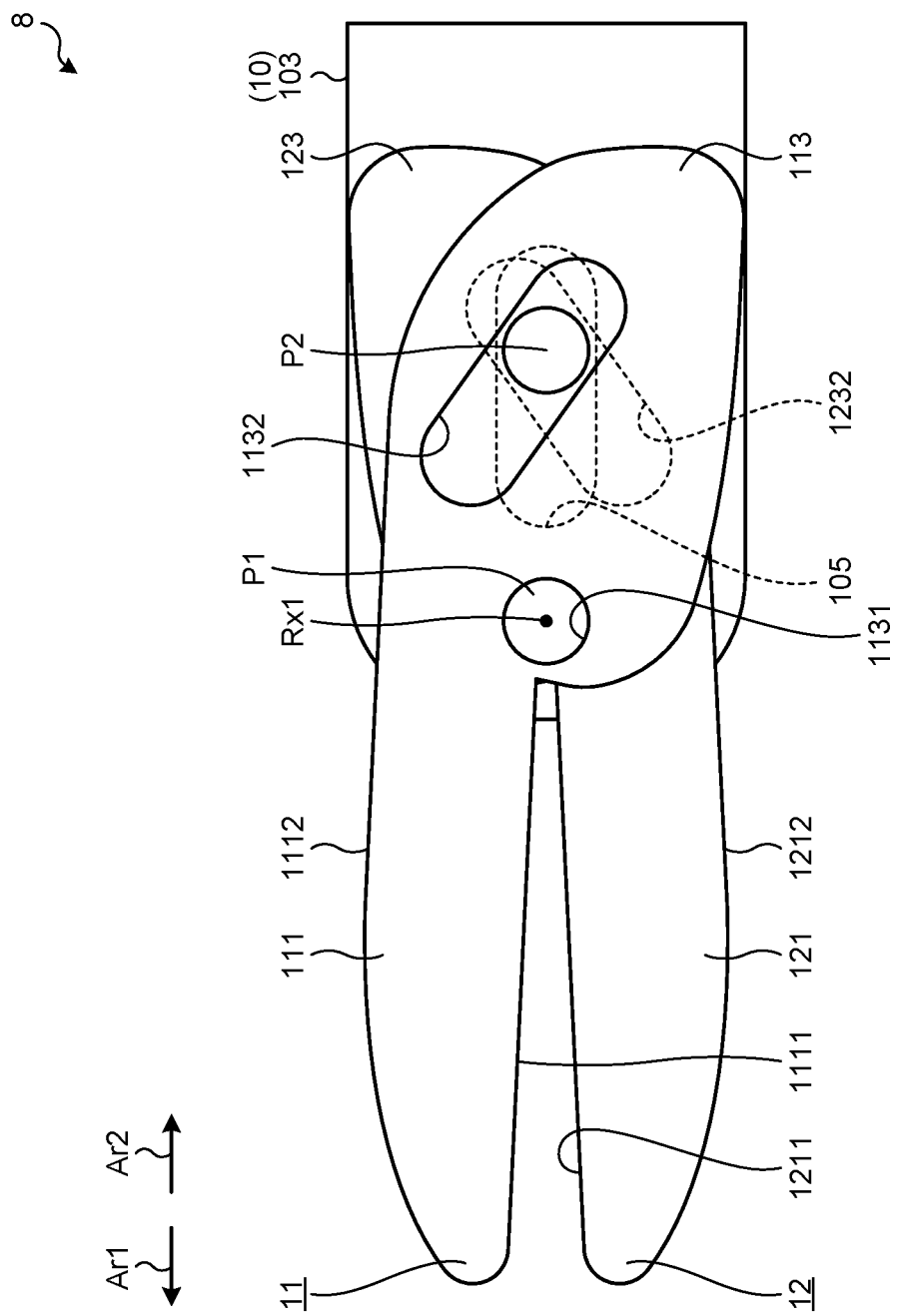
FIG. 3 is a view illustrating the configuration of the gripping portion.
Figure 4:
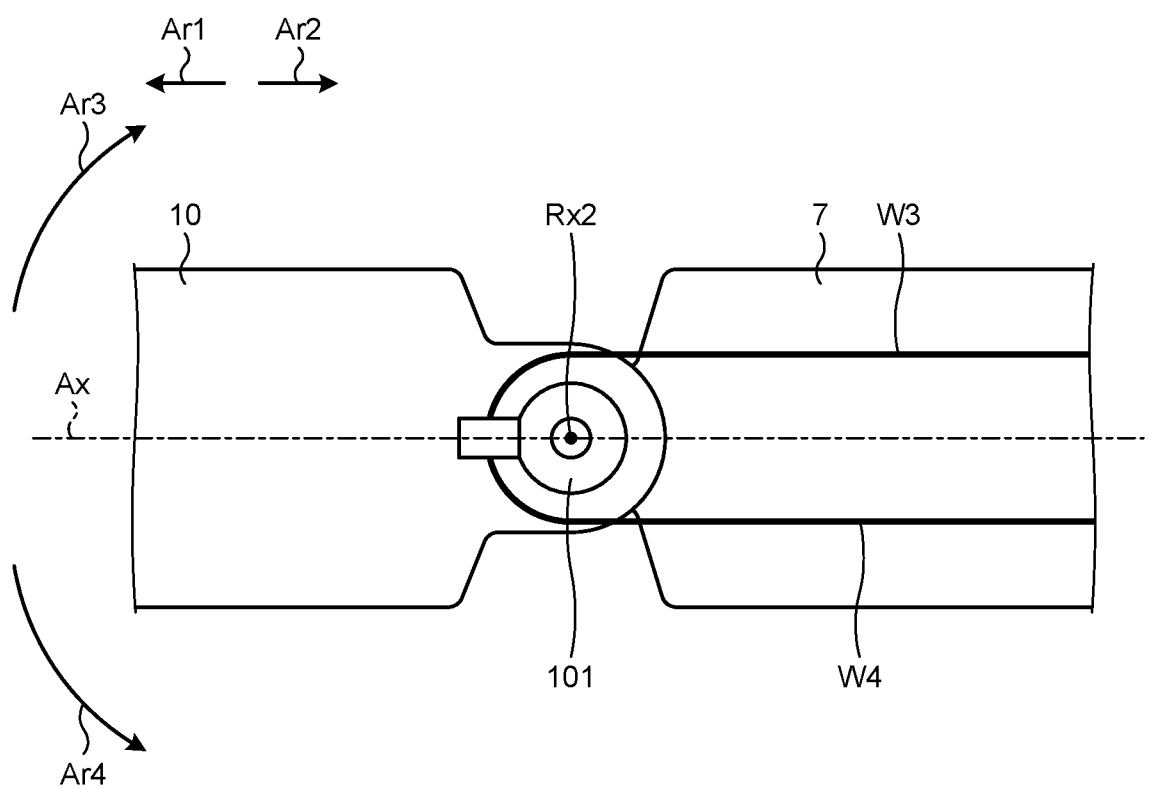
FIG. 4 is a view illustrating the configuration of the gripping portion.

FIGS. 2 to 4 are views illustrating a configuration of the gripping portion 8. Specifically, FIG. 2 is a perspective view of the gripping portion 8. FIG. 3 is a view of the gripping portion 8 as viewed along a first rotation axis Rx1. In FIG. 3, for convenience of explanation, illustration of a first shaft support portion 102 is omitted. FIG. 4 is a view of a connection portion between the shaft 7 and a base portion 10 as viewed along a second rotation axis Rx2.

As illustrated in FIGS. 2 to 4, the gripping portion 8 includes the base portion 10 and the first and second gripping pieces 11 and 12.

The base portion 10 has a tubular shape. In the base portion 10, an end portion (an end portion on the proximal end side Ar2) on one end side of the cylindrical shape is pivotally supported with respect to an end portion on the distal end side Ar1 of the shaft 7 so as to be rotatable about the second rotation axis Rx2. The second rotation axis Rx2 is an axis orthogonal to the central axis Ax.

More specifically, as illustrated in FIG. 4, the base portion 10 is provided with a pulley 101 coaxial with the second rotation axis Rx2. One end of each of the third and fourth wires W3 and W4 constituting the bending mechanism described above is fixed to an outer peripheral surface of the pulley 101.

Then, when the bending operation portion 5 is rotated in a first direction (bending operation) by the operator, the third wire W3 moves toward the proximal end side Ar2. Meanwhile, the fourth wire W4 moves toward the distal end side Ar1. As a result, the gripping portion 8 rotates in a first bending direction Ar3 (FIGS. 2 and 4) about the second rotation axis Rx2 with respect to the shaft 7.

Meanwhile, in a case where the bending operation portion 5 is rotated (bent) in the second direction that is the direction opposite to the first direction described above by the operator, the third and fourth wires W3 and W4 operate in the directions opposite to the above. As a result, the gripping portion 8 rotates about the second rotation axis Rx2 with respect to the shaft 7 in a second bending direction Ar4 (FIGS. 2 and 4) which is a direction opposite to the first bending direction Ar3.

In the base portion 10, as illustrated in FIG. 2, first and second shaft support portions 102 and 103 protruding toward the distal end side Ar1 are provided at an end portion (end portion on the distal end side Ar1) on the other end side of the cylindrical shape.

Each of the first and second shaft support portions 102 and 103 has an elongated substantially flat plate shape. The first and second shaft support portions 102 and 103 are opposed to each other in a direction in which a longitudinal direction thereof is along the central axis of the tubular shape of the base portion 10 and along the first rotation axis Rx1. The first rotation axis Rx1 is an axis orthogonal to the central axis of the tubular shape of the base portion 10.

As illustrated in FIG. 2, circular bearing holes 104 penetrating front and back surfaces of the first and second shaft support portions 102 and 103 are formed in the first and second shaft support portions 102 and 103, respectively. A columnar bearing pin P1 having the first rotation axis Rx1 as a central axis is inserted into the bearing hole 104.

Further, in the first and second shaft support portions 102 and 103, as illustrated in FIG. 2 or 3, track holes 105 penetrating the front and back of the first and second shaft support portions 102 and 103 and extending along the longitudinal direction of the first and second shaft support portions 102 and 103 are formed on the proximal end side Ar2 with respect to the bearing hole 104. An opening/closing pin P2 constituting the above-described opening/closing mechanism is inserted into the track hole 105.

Figure 5:
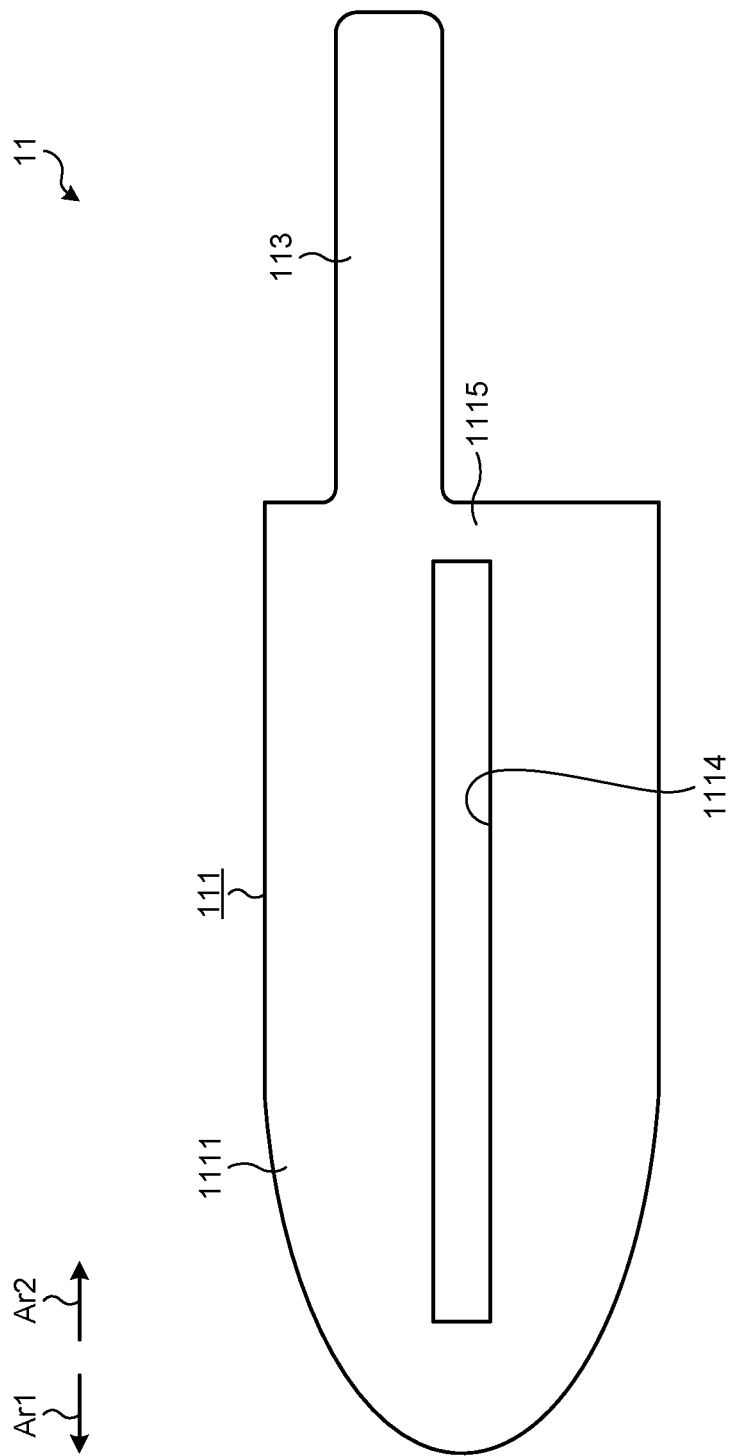
FIG. 5 is a view illustrating a configuration of a first gripping piece.
Figure 6:
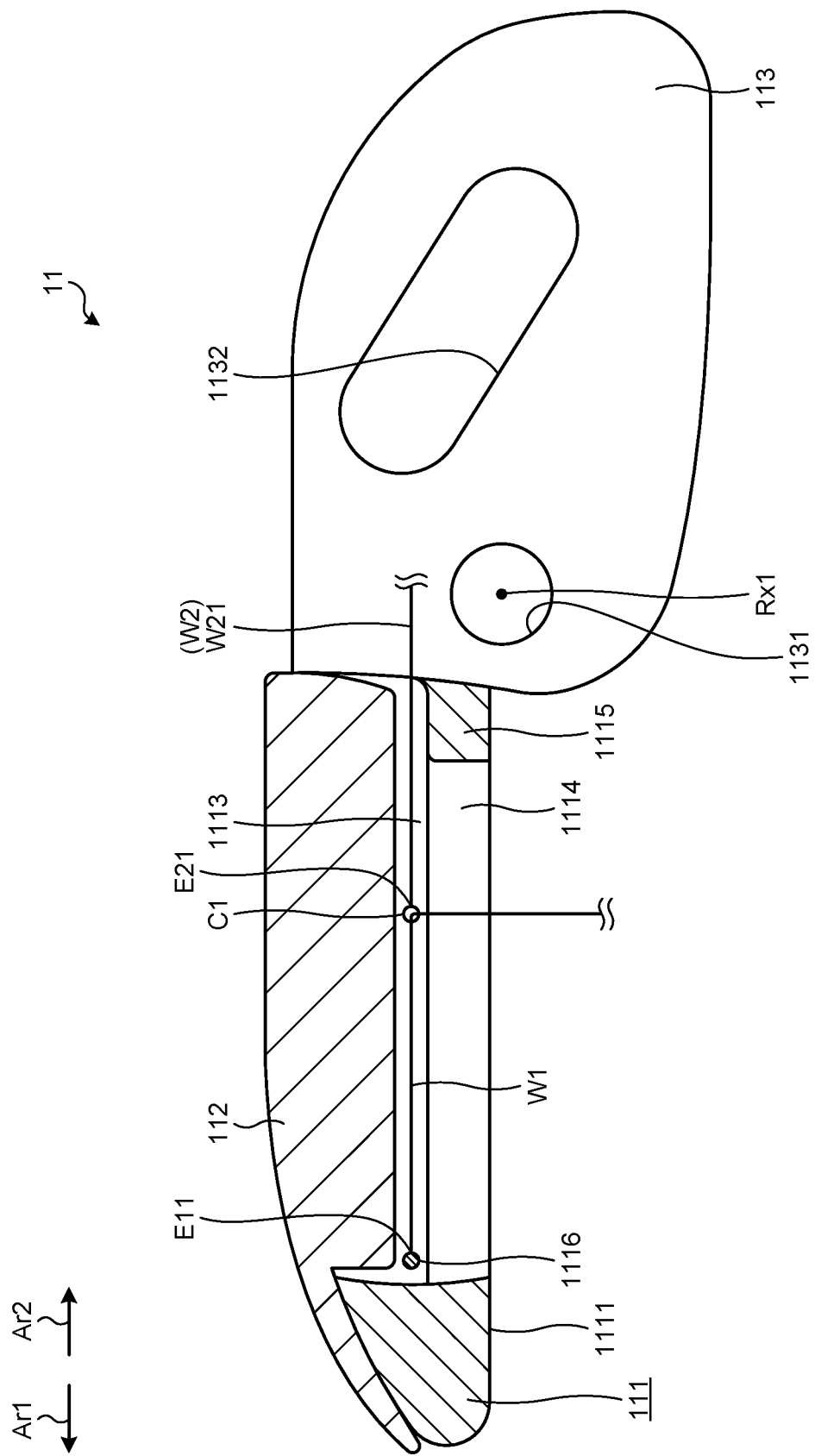
FIG. 6 is a view illustrating the configuration of the first gripping piece.
Figure 7:
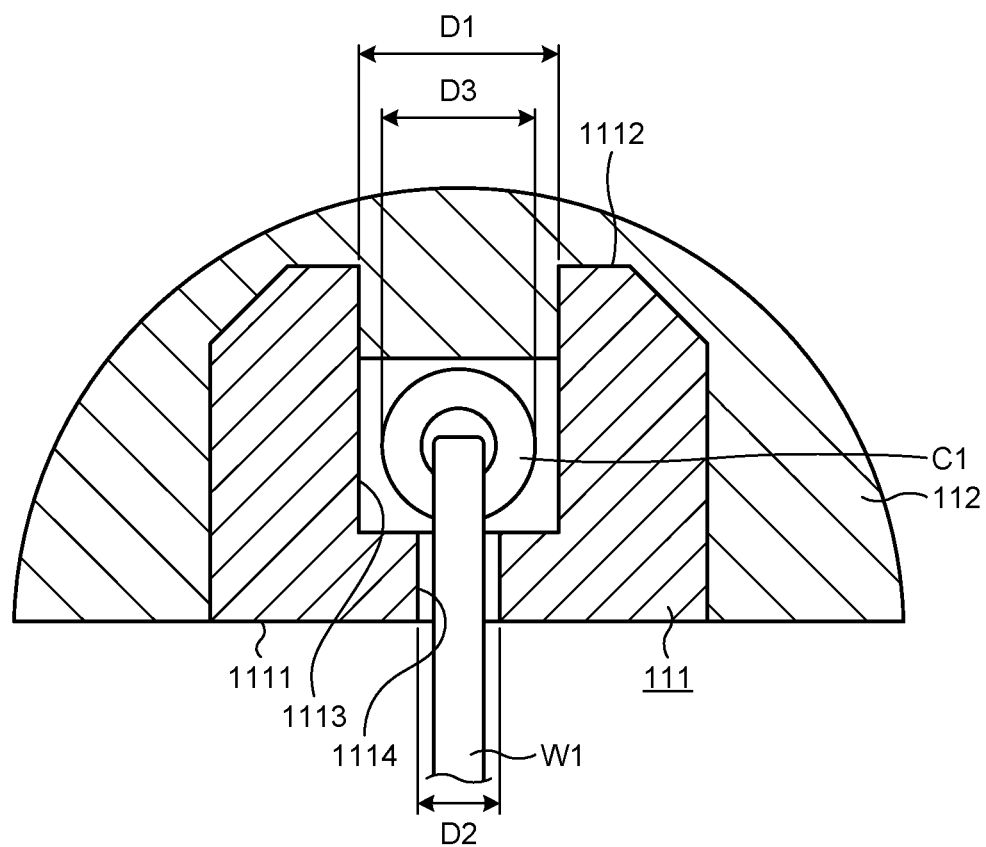
FIG. 7 is a view illustrating the configuration of the first gripping piece.

FIGS. 5 to 7 are views illustrating a configuration of the first gripping piece 11. Specifically, FIG. 5 is a view of the first gripping piece 11 as viewed from a first gripping surface 1111 side. FIG. 6 is a view of the first gripping piece 11 as viewed along the first rotation axis Rx1. In FIG. 6, for convenience of description, only a first gripping piece body 111 and a first cover portion 112 of the first gripping piece 11 are cut by a plane including a tubular central axis of the base portion 10. FIG. 7 is a cross-sectional view of the first gripping piece 11 taken along a plane orthogonal to the tubular central axis of the base portion 10.

The first gripping piece 11 is a part rotatably supported by the bearing pin P1 with respect to the first and second shaft support portions 102 and 103. As illustrated in FIG. 2, 3, 5, or 6, the first gripping piece 11 includes a first gripping piece body 111, a first cover portion 112 (FIG. 6), and a first attachment portion 113.

The first gripping piece body 111 has an elongated substantially flat plate shape. In the first gripping piece body 111, one plate surface functions as a first gripping surface 1111 (FIGS. 3 and 5 to 7) that grips the target site with the second gripping piece 12.

In the first gripping piece body 111, as illustrated in FIG. 6 or 7, a first accommodation hole 1113 recessed toward the first gripping surface 1111 is formed in a first back surface 1112 formed on the front and back sides of the first gripping surface 1111. The first accommodation hole 1113 extends linearly along the longitudinal direction of the first gripping piece body 111 from the proximal end toward the distal end of the first gripping piece body 111.

In the first gripping piece body 111, as illustrated in FIGS. 5 to 7, a first communication hole 1114 recessed toward the first back surface 1112 is formed in the first gripping surface 1111. The first communication hole 1114 extends linearly along the longitudinal direction of the first gripping piece body 111 and communicates with the first accommodation hole 1113. As illustrated in FIG. 5 or 6, the first communication hole 1114 does not penetrate to the proximal end of the first gripping piece body 111. Hereinafter, a site closer to the proximal end side Ar2 than the first communication hole 1114 is referred to as a first positioning portion 1115 (FIGS. 5 and 6).

Here, as illustrated in FIG. 7, the first communication hole 1114 is located at the center of the first accommodation hole 1113 in a width direction (right-left direction in FIG. 7), and has a width dimension D2 smaller than the width dimension D1 of the first accommodation hole 1113.

The first cover portion 112 is attached to the first gripping piece body 111 in a state of covering the outer surface other than the first gripping surface 1111 and the proximal end among all the outer surfaces of the first gripping piece body 111. In FIGS. 2 and 3, illustration of the first cover portion 112 is omitted for convenience of description.

The first attachment portion 113 is a part for attaching the first gripping piece 11 to the base portion 10. The first attachment portion 113 has an elongated substantially flat plate shape, and is integrally formed with the proximal end side Ar2 of the first gripping piece body 111 and one side in the width direction (direction along the first rotation axis Rx1) in a posture in which the longitudinal direction is along the longitudinal direction of the first gripping piece body 111 and is orthogonal to the first gripping surface 1111.

As illustrated in FIG. 6, the first attachment portion 113 is formed with a first circular hole 1131 penetrating the front and back of the first attachment portion 113. The bearing pin P1 is inserted into the first circular hole 1131 in a posture in which the first attachment portion 113 abuts on the inner surface of the first shaft support portion 102, whereby the first gripping piece 11 is pivotally supported rotatably about the first rotation axis Rx1 with respect to the base portion 10.

In the first attachment portion 113, a first opening/closing guide hole 1132 penetrating the front and back of the first attachment portion 113 is formed on the proximal end side Ar2 of the first circular hole 1131. The first opening/closing guide hole 1132 is a track hole inclined upward in FIG. 6 toward the first circular hole 1131. The opening/closing pin P2 is inserted into the first opening/closing guide hole 1132.

Figure 8:
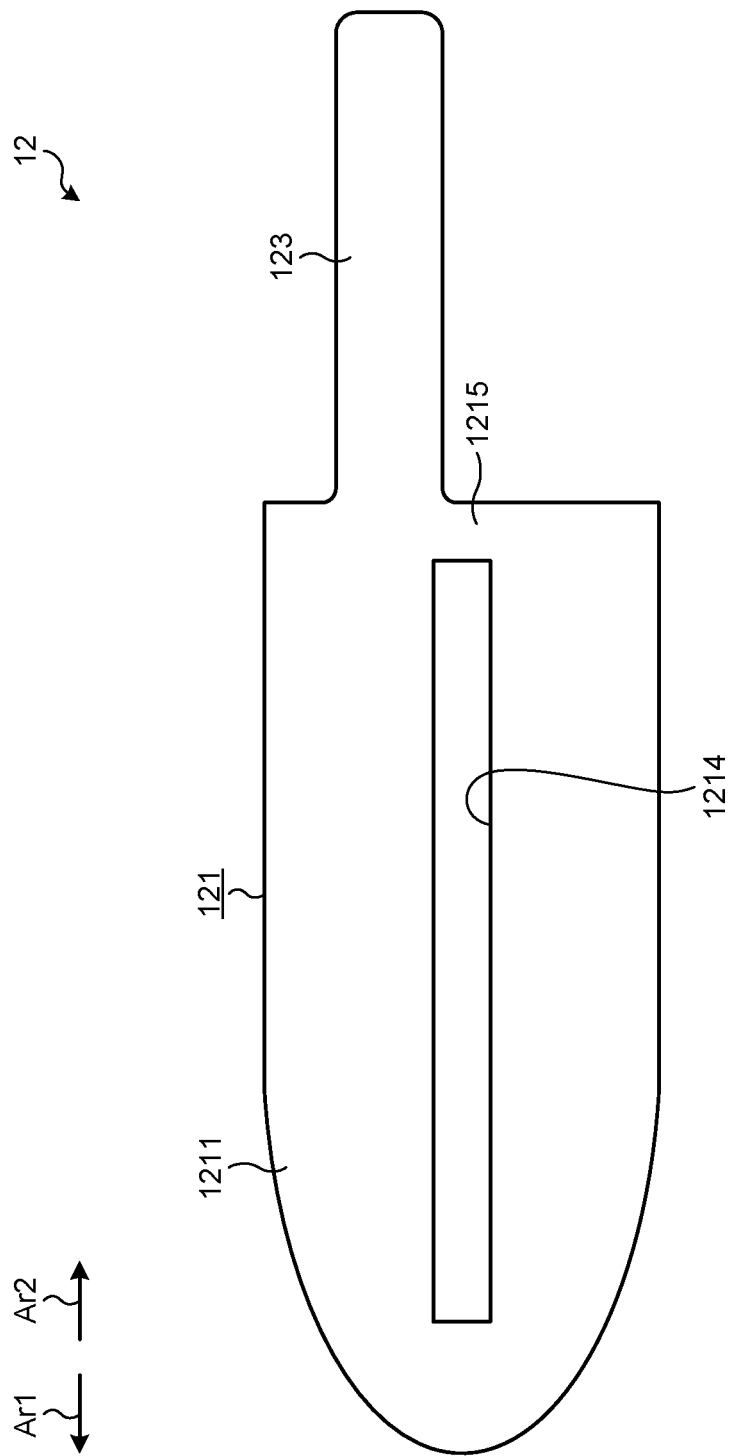
FIG. 8 is a view illustrating a configuration of a second gripping piece.
Figure 9:
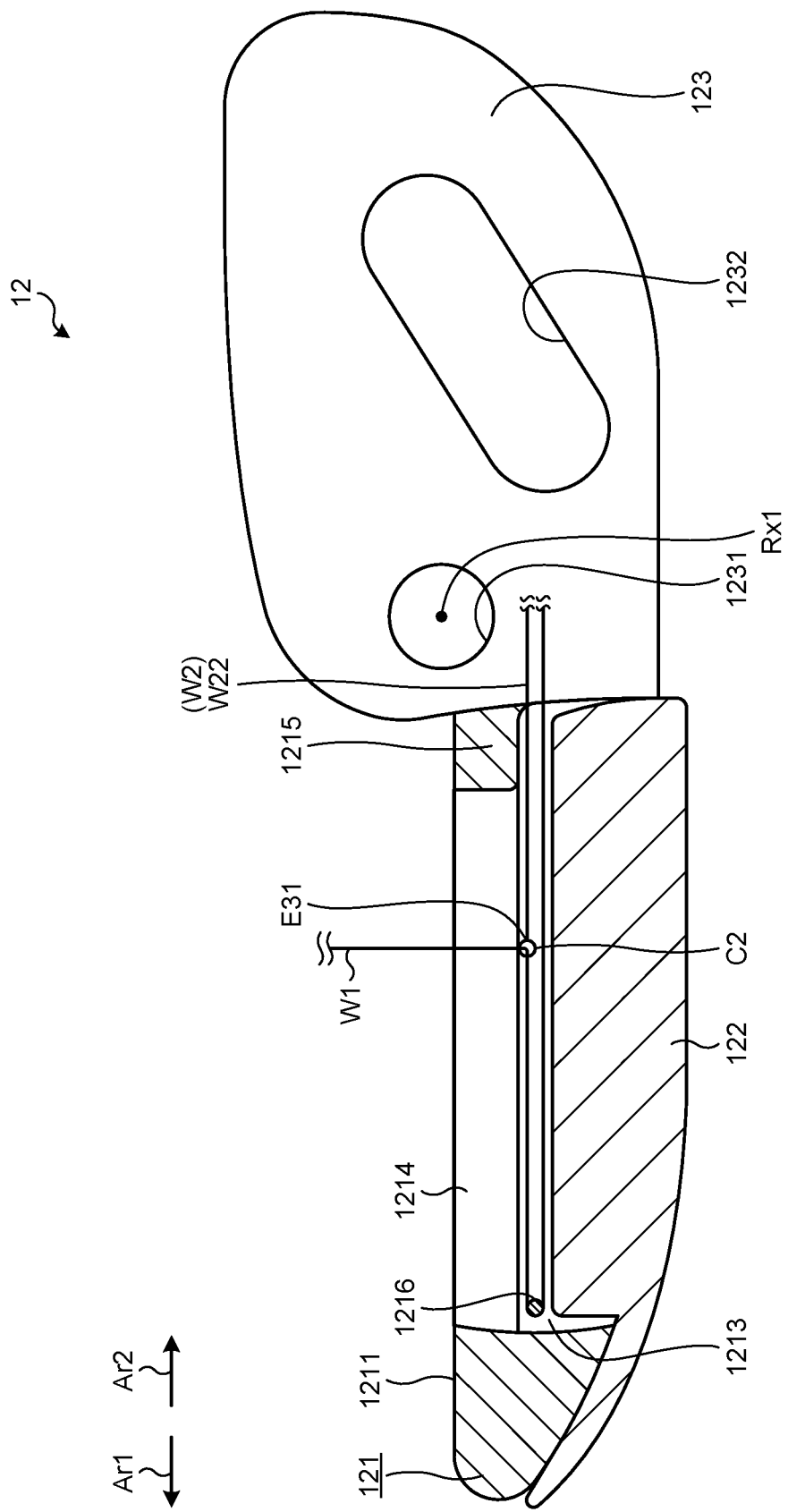
FIG. 9 is a view illustrating the configuration of the second gripping piece.
Figure 10:
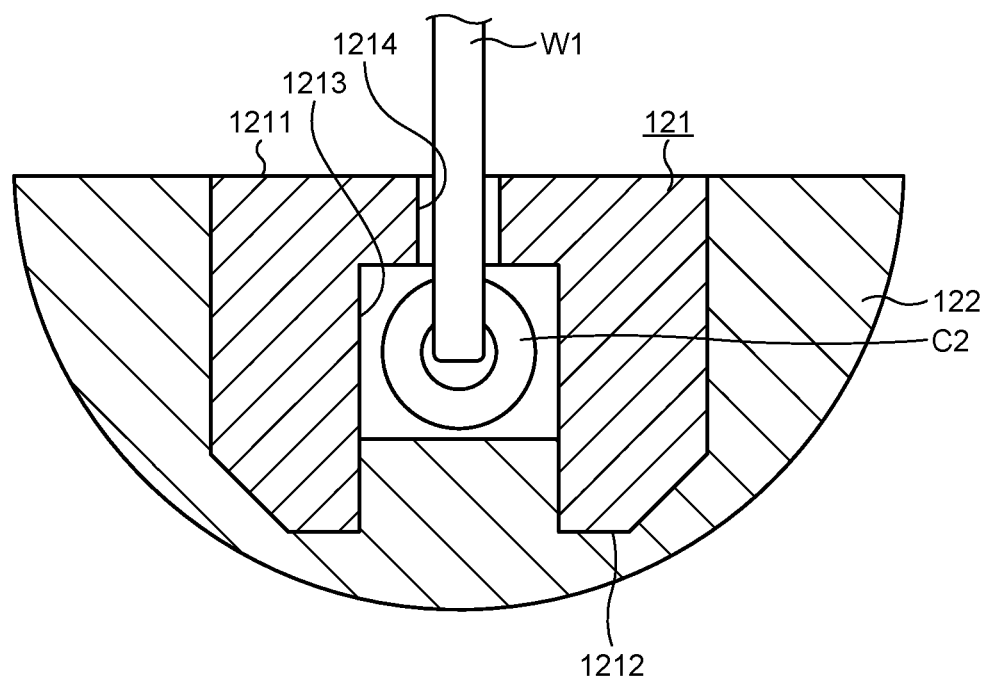
FIG. 10 is a view illustrating the configuration of the second gripping piece.

FIGS. 8 to 10 are views illustrating a configuration of the second gripping piece 12. Specifically, FIGS. 8 to 10 are views corresponding to FIGS. 5 to 7, respectively.

As illustrated in FIGS. 8 to 10, the second gripping piece 12 has the same configuration and shape as those of the first gripping piece 11. That is, the second gripping piece 12 includes a second gripping piece body 121 (includes a second gripping surface 1211, a second back surface 1212, a second accommodation hole 1213, a second communication hole 1214, and a second positioning portion 1215), a second cover portion 122, and a second attachment portion 123 (including a second circular hole 1231 and a second opening/closing guide hole 1232) similar to the first gripping piece body 111 (includes a first gripping surface 1111, a first back surface 1112, a first accommodation hole 1113, a first communication hole 1114, and a first positioning portion 1115), the first cover portion 112, and the first attachment portion 113 (including the first circular hole 1131 and the first opening/closing guide hole 1132) of the first gripping piece 11.

Then, the bearing pin P1 is inserted into the second circular hole 1231 in a state where the second attachment portion 123 abuts on the inner surface of the second shaft support portion 103, whereby the second gripping piece 12 is pivotally supported rotatably about the first rotation axis Rx1 with respect to the base portion 10. In this state, the opening/closing pin P2 is inserted into the second opening/closing guide hole 1232.

When the operator rotates (opening/closing operation) the first movable handle 3 in a direction approaching the fixed handle 22, the opening/closing pin P2 moves from the distal end side Ar1 toward the proximal end side Ar2 inside the track hole 105 and the first and second opening/closing guide holes 1132 and 1232. Then, the first gripping piece 11 rotates counterclockwise in FIG. 3 about the first rotation axis Rx1 with respect to the base portion 10 as the edge portion of the first opening/closing guide hole 1132 is pressed by the opening/closing pin P2. Meanwhile, the second gripping piece 12 rotates clockwise in FIG. 3 about the first rotation axis Rx1 with respect to the base portion 10 as the edge portion of the second opening/closing guide hole 1232 is pressed by the opening/closing pin P2. As a result, the first and second gripping pieces 11 and 12 finally enter a "closed state" in which the first and second gripping surfaces 1111 and 1211 are close to each other (FIG. 3).

Meanwhile, in a case where the first movable handle 3 is rotated (opening/closing operation) in a direction away from the fixed handle 22 by the operator, the opening/closing pin P2 and the first and second gripping pieces 11 and 12 operate in a direction opposite to the above. As a result, the first and second gripping pieces 11 and 12 are in an "open state" in which the first and second gripping surfaces 1111 and 1211 are separated from each other.

Configurations of First and Second Wires

Next, the configurations of the first and second wires W1 and W2 will be described.

Figure 11:
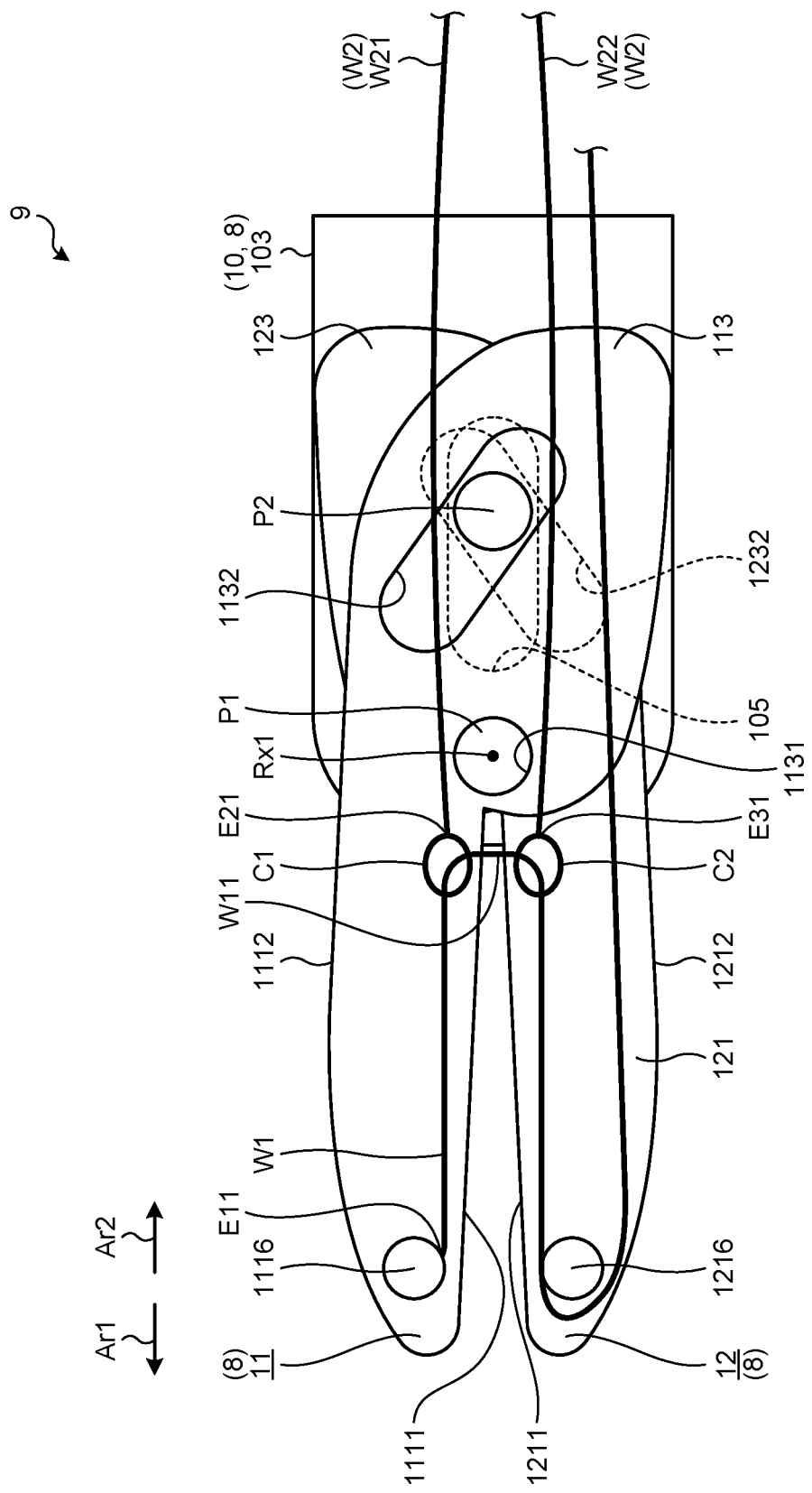
FIG. 11 is a view for explaining arrangement positions of first and second wires.
Figure 12:
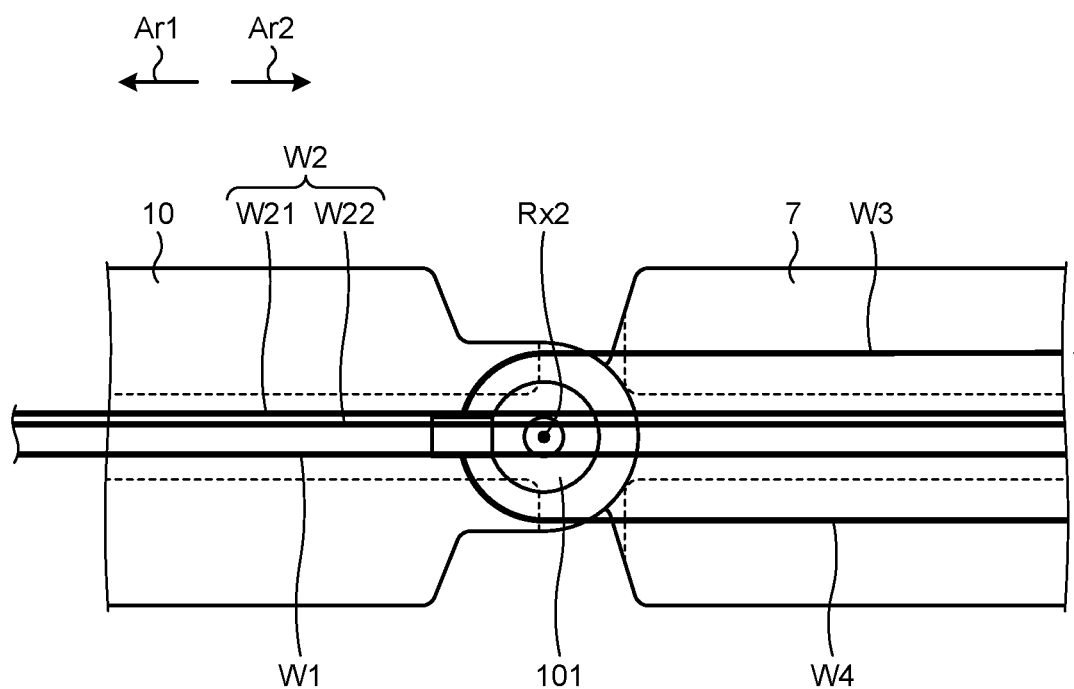
FIG. 12 is a view for explaining the arrangement positions of the first and second wires.
Figure 13:
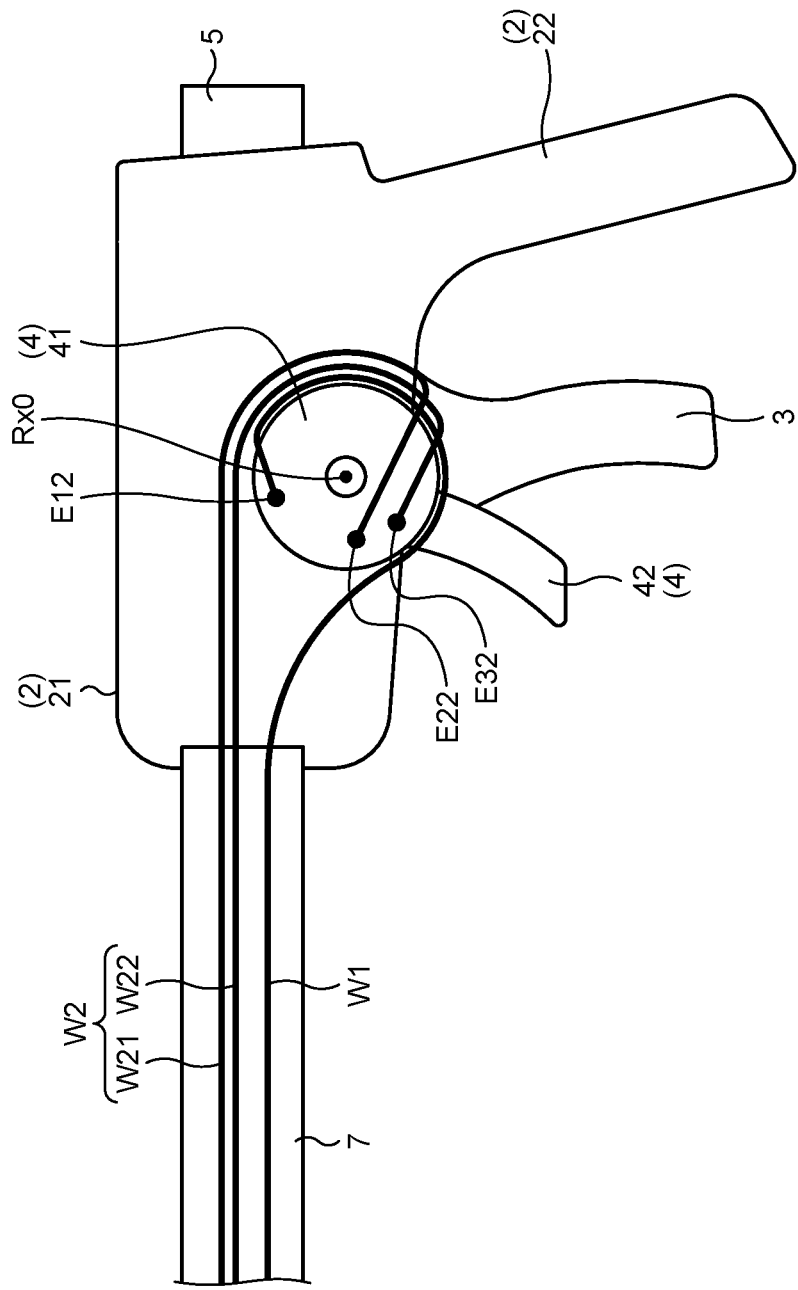
FIG. 13 is a view for explaining the arrangement positions of the first and second wires.

FIGS. 11 to 13 are views for explaining arrangement positions of the first and second wires W1 and W2. Specifically, FIG. 11 is a view corresponding to FIG. 3, and is a view illustrating a state in which the first and second wires W1 and W2 are routed inside the gripping portion 8. In FIG. 11, for convenience of explanation, illustration of the first and second accommodation holes 1113 and 1213 and the first and second communication holes 1114 and 1214 is omitted. FIG. 12 is a view corresponding to FIG. 4, and is a view illustrating a state in which the first and second wires W1 and W2 are routed inside the base portion 10 and the shaft 7. FIG. 13 is a view illustrating a state in which the first and second wires W1 and W2 are routed inside the shaft 7 and the housing 2. In FIG. 13, for convenience of explanation, illustration of the rotary knob 6 is omitted.

In the first embodiment, the first wire W1 is made of a resin material. An outer diameter dimension of the first wire W1 is, for example, 0.5 mm or less.

Of a first end E11 and a second end E12 which are both ends of the first wire W1, the first end E11 is fixed to the first gripping piece 11 as illustrated in FIG. 6 or 11.

Specifically, in the first gripping piece body 111, as illustrated in FIG. 6 or 11, a fixed shaft portion 1116 extending in parallel with the first rotation axis Rx1 is attached to the distal end side Ar1 inside the first accommodation hole 1113. The first end E11 is fixed to the fixed shaft portion 1116. As illustrated in FIG. 6, FIG. 7, or FIG. 11, the first wire W1 is routed from the fixed shaft portion 1116 toward the proximal end side Ar2 inside the first accommodation hole 1113, and is routed toward the second gripping piece 12 through the first communication hole 1114.

In the second gripping piece body 121, as illustrated in FIG. 9 or 11, a columnar support shaft 1216 extending in parallel with the first rotation axis Rx1 is attached to the distal end side Ar1 inside the second accommodation hole 1213. Note that the support shaft 1216 may be attached to the second gripping piece body 121 so as to be rotatable about a columnar central axis of the support shaft 1216, or may be attached so as not to be rotatable.

Then, as illustrated in FIGS. 9 to 11, the first wire W1 routed from the first gripping piece 11 toward the second gripping piece 12 is routed inside the second accommodation hole 1213 through the second communication hole 1214. That is, the first wire W1 is bridged between the first and second gripping surfaces 1111 and 1211. In addition, the first wire W1 is routed toward the distal end side Ar1 inside the second accommodation hole 1213, folded back at the support shaft 1216, and again routed toward the proximal end side Ar2. That is, the first wire W1 is routed toward the proximal end side Ar2 in a state where a portion between the first end E11 and the second end E12 is hooked by the support shaft 1216.

Then, the first wire W1 routed toward the proximal end side Ar2 inside the second accommodation hole 1213 is pulled out from the proximal end of the second gripping piece body 121 to the outside of the second accommodation hole 1213. As illustrated in FIG. 12, the first wire W1 drawn out to the outside of the second accommodation hole 1213 is routed from the distal end side Ar1 toward the proximal end side Ar2 inside the base portion 10 and the shaft 7. Further, the first wire W1 routed toward the proximal end side Ar2 inside the shaft 7 is routed inside the housing main body 21 and wound around the outer peripheral surface of the base portion 41 counterclockwise in FIG. 13. The second end E12 is fixed to the base portion 41.

In the first embodiment, two second wires W2 are provided. The second wire W2 may be made of the same material as the first wire W1, or may be made of a different material (for example, a metal material or the like). An outer diameter dimension of the second wire W2 is, for example, 0.5 mm or less.

Hereinafter, one of the two second wires W2 will be referred to as a second wire W21, and the other will be referred to as a second wire W22.

Of a first end E21 and a second end E22 which are both ends of the second wire W21, the first end E21 is provided with a first connection portion C1 as illustrated in FIG. 6, 7, or 11. The first connection portion C1 corresponds to a connector. The first connection portion C1 is a ring-shaped portion through which the first wire W1 is inserted. That is, the first connection portion C1 is connected to the first wire W1 so as to be relatively movable.

Here, as illustrated in FIG. 7, an outer diameter dimension D3 of the first connection portion C1 is smaller than the width dimension D1 of the first accommodation hole 1113 and larger than the width dimension D2 of the first communication hole 1114.

Then, as illustrated in FIG. 6, FIG. 7, or FIG. 11, the second wire W21 is routed from the distal end side Ar1 toward the proximal end side Ar2 inside the first accommodation hole 1113 with the first connection portion C1 positioned inside the first accommodation hole 1113, and is routed out from the proximal end of the first gripping piece body 111 to the outside of the first accommodation hole 1113. As illustrated in FIG. 12, similarly to the first wire W1, the second wire W21 drawn out to the outside of the first accommodation hole 1113 is routed from the distal end side Ar1 toward the proximal end side Ar2 inside the base portion 10 and the shaft 7. Further, the second wire W21 routed toward the proximal end side Ar2 inside the shaft 7 is routed inside the housing main body 21 and wound around the outer peripheral surface of the base portion 41 in the clockwise direction in FIG. 13. The second end E22 is fixed to the base portion 41.

Of a first end E31 and a second end E32 which are both ends of the second wire W22, the first end E31 is provided with a second connection portion C2 having the same shape as the first connection portion C1 as illustrated in FIGS. 9 to 11. The second connection portion C2 corresponds to a connector. Then, the first wire W1 is inserted into the second connection portion C2. That is, the second connection portion C2 is connected to the first wire W1 so as to be relatively movable.

Then, as illustrated in FIGS. 9 to 11, the second connection portion C2 is located inside the second accommodation hole 1213, the second wire W22 is routed from the distal end side Ar1 toward the proximal end side Ar2 inside the second accommodation hole 1213, and is pulled out from the proximal end of the second gripping piece body 121 to the outside of the second accommodation hole 1213. As illustrated in FIG. 12, similarly to the first and second wires W1 and W21, the second wire W22 drawn out to the outside of the second accommodation hole 1213 is routed from the distal end side Ar1 toward the proximal end side Ar2 inside the base portion 10 and the shaft 7. Further, the second wire W22 routed toward the proximal end side Ar2 inside the shaft 7 is routed inside the housing main body 21 and wound around the outer peripheral surface of the base portion 41 in the clockwise direction in FIG. 13. Then, the second end E32 is fixed to the base portion 41.

Operations of First and Second Wires

Figure 14:
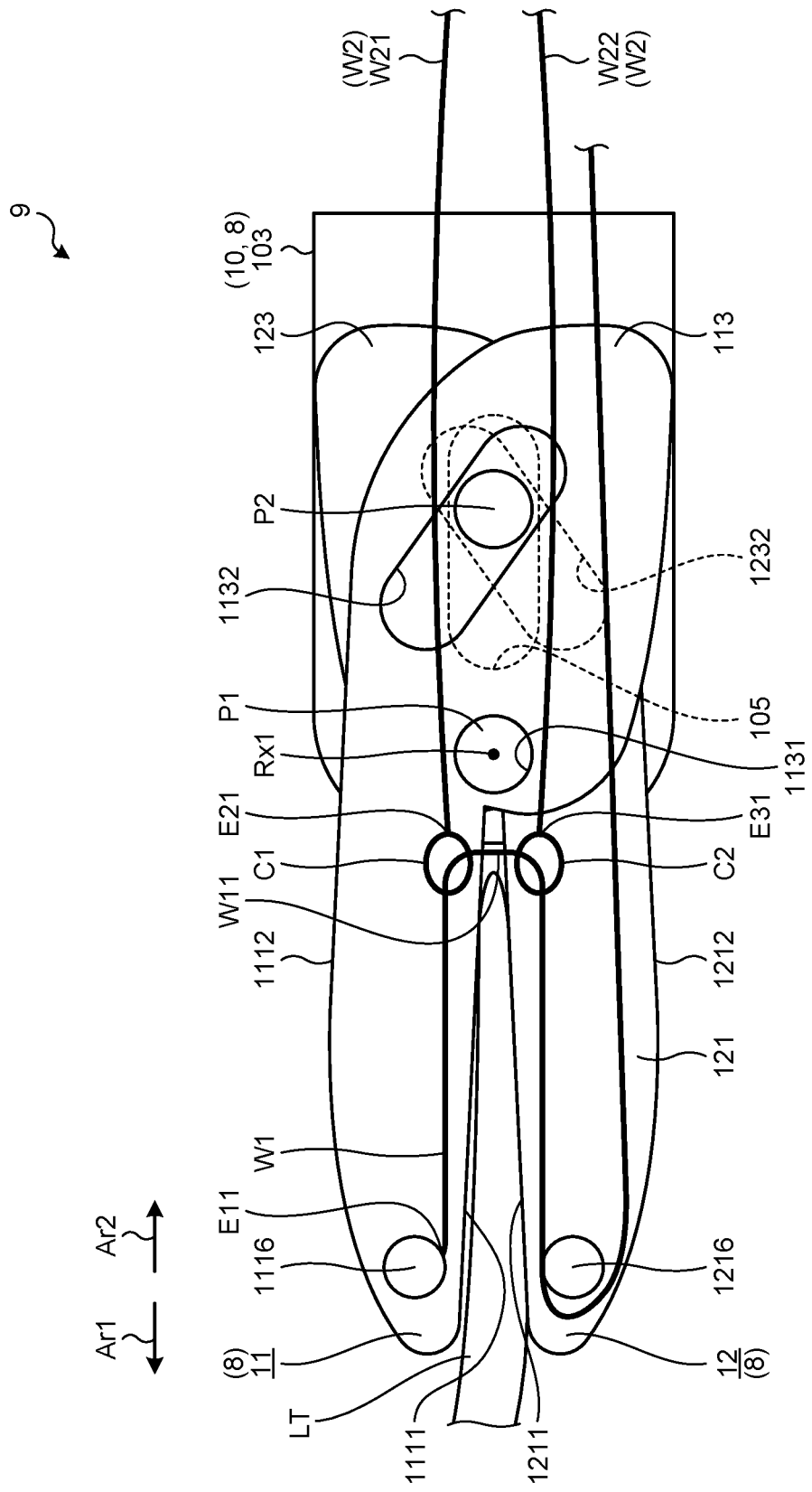
FIG. 14 is a view for explaining operations of the first and second wires.
Figure 15:
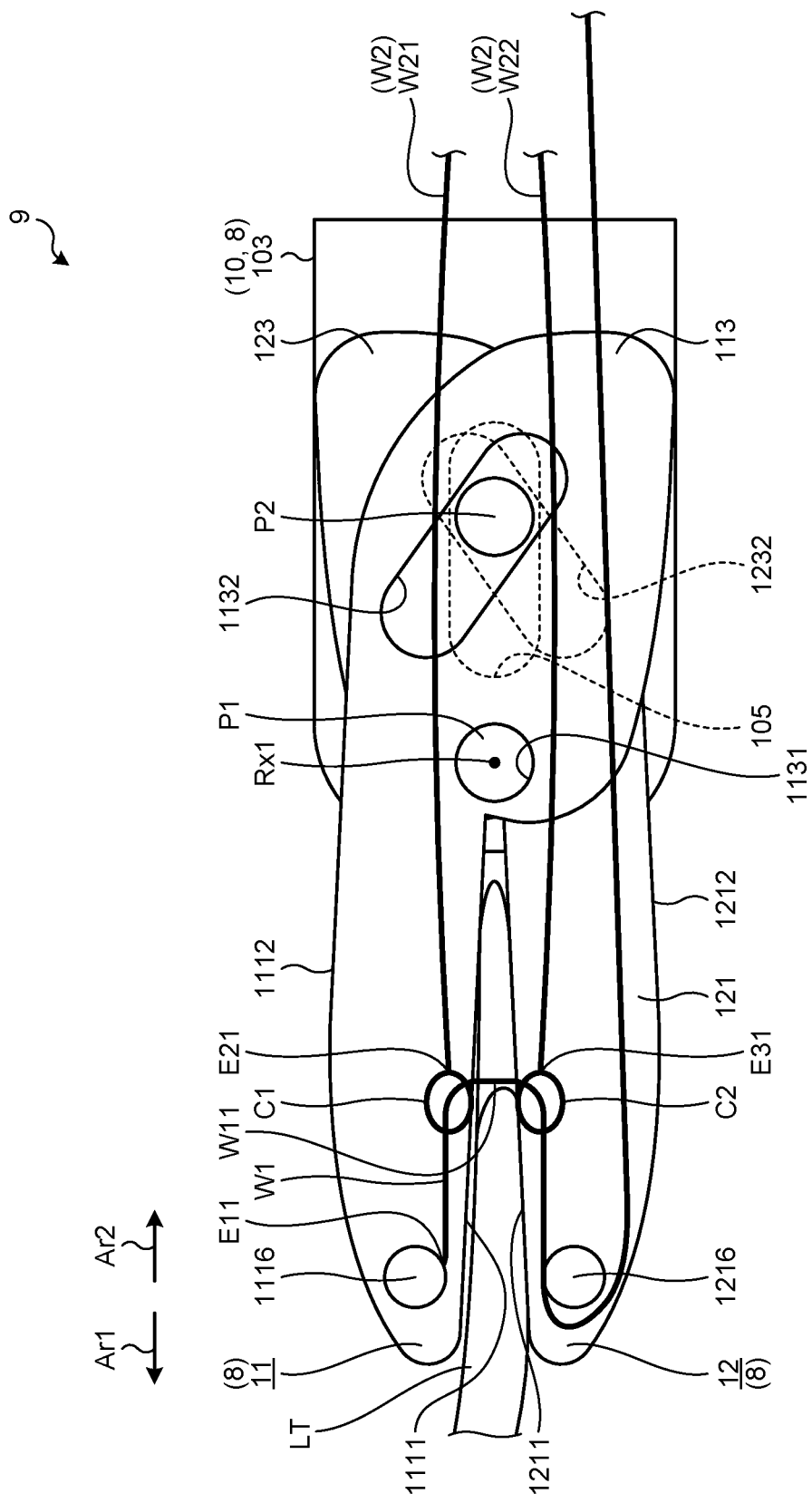
FIG. 15 is a view for explaining the operations of the first and second wires.

FIGS. 14 and 15 are views for explaining operations of the first and second wires W1 and W2. Specifically, FIGS. 14 and 15 are views corresponding to FIG. 11, and illustrate a state in which a target site LT is gripped between the first and second gripping surfaces 1111 and 1211.

In a case where the second movable handle 4 is rotated (incision-operated) in a direction approaching the fixed handle 22 by the operator, the portion of the first wire W1 on the second end E12 side is wound around the outer peripheral surface of the base portion 41 and pulled toward the proximal end side Ar2. Meanwhile, the winding of the two second wires W21 and W22 around the outer peripheral surface of the base portion 41 at each portion on the sides of the second ends E22 and E32 is loosened. As a result, in the first wire W1, the portion W11 (hereinafter, referred to as an incision portion W11) bridged between the first and second gripping surfaces 1111 and 1211 moves from the first position illustrated in FIG. 14 toward the distal end side Ar1 as illustrated in FIG. 15. Then, the target site LT is incised by the incision portion W11.

Meanwhile, when the operator releases his/her hand from the second movable handle 4, the second movable handle 4 rotates in a direction away from the fixed handle 22 by the biasing force of the spring. In this case, the winding of the first wire W1 around the outer peripheral surface of the base portion 41 at the portion on the second end E12 side is loosened. Meanwhile, each portion of the two second wires W21 and W22 on the sides of the second ends E22 and E32 is wound around the outer peripheral surface of the base portion 41 and pulled toward the proximal end side Ar2. As a result, the incision portion W11 is returned from the position illustrated in FIG. 15 to the first position illustrated in FIG. 14.

According to the above-described first embodiment, the following effects are obtained.

In the gripping device 9 according to the first embodiment, the first wire W1 causes the incision portion W11 to move from the first position illustrated in FIG. 14 toward the distal end of the gripping portion 8 according to the pulling of the second end E12, and incises the target site LT gripped between the first and second gripping surfaces 1111 and 1211.

That is, since the first wire W1 is pulled when the target site LT is incised by the first wire W1, rigidity of the first wire W1 can be reduced as compared with a configuration in which the first wire W1 is pushed. In other words, the first wire W1 can be thinned. Therefore, the size of the gripping device 9 can be reduced by adopting the thin first wire W1.

Meanwhile, in a case where the plurality of first wires W1 are routed to the connection portion (joint portion) between the base portion 10 and the shaft 7, the joint portion becomes thick, which results in hindering reduction in size of the distal end portion of the treatment tool 1.

In the gripping device 9 according to the first embodiment, the first end E11 of the first wire W1 is fixed to the fixed shaft portion 1116. That is, only one first wire W1 is routed from the inside of the base portion 10 to the inside of the shaft 7. Therefore, the size of the distal end portion of the treatment tool 1 can be further reduced.

In particular, in the configuration in which the first end E11 is fixed to the fixed shaft portion 1116 and the target site LT is incised in accordance with the pulling of the second end E12, the incision portion W11 slides downward in FIGS. 14 and 15 in accordance with the pulling of the second end E12 and is always changed to a new site. That is, since the target site LT can be incised while the incision portion W11 is slid, the target site LT can be smoothly incised even when an operation force (force for pulling the second end E12) is small.

In addition, the gripping device 9 according to the first embodiment includes the second wire W2 described above.

Therefore, the incision portion W11 can be returned to the first position by the second wire W2. That is, the incision can be performed a plurality of times, and convenience can be improved.

When the second wire W2 is unmovably fixed to the first wire W1, the following problem may occur.

That is, when the target site LT is incised by the first wire W1, the connection portion of the first and second wires W1 and W2 mechanically interferes with the target site LT, and there is a possibility that the incision performance of the target site LT is deteriorated.

In the gripping device 9 according to the first embodiment, the second wire W2 is connected to be relatively movable with respect to the first wire W1 by the first and second connection portions C1 and C2. Therefore, there is no possibility that the above-described problem occurs.

In addition, in the gripping device 9 according to the first embodiment, the outer diameter dimension D3 of the first and second connection portions C1 and C2 is smaller than the width dimension D1 of the first and second accommodation holes 1113 and 1213 and larger than the width dimension D2 of the first and second communication holes 1114 and 1214.

Therefore, it is possible to prevent the first and second connection portions C1 and C2 from coming out between the first and second gripping surfaces 1111 and 1211 through the first and second communication holes 1114 and 1214. Therefore, the portion of the first wire W1 other than the incision portion W11 can be accommodated in the first and second accommodation holes 1113 and 1213 by the first and second connection portions C1 and C2, and the portion other than the incision portion W11 and the second wire W2 can be prevented from coming out between the first and second gripping surfaces 1111 and 1211.

Here, it is assumed that the first and second connection portions C1 and C2 come out of the proximal ends of the first and second gripping piece bodies 111 and 121 to the outside of the first and second accommodation holes 1113 and 1213 by pulling the second wire W2.

In this case, in the gripping device 9 according to the first embodiment, since the first and second positioning portions 1115 and 1215 are provided in the first and second gripping pieces 11 and 12, when the first wire W1 is pulled, the first and second connection portions C1 and C2 always enter the first and second accommodation holes 1113 and 1213 from the proximal ends of the first and second gripping piece bodies 111 and 121. Therefore, the above-described effect of "the portion of the first wire W1 other than the incision portion W11 and the second wire W2 can be prevented from coming out between the first and second gripping surfaces 1111 and 1211" can be suitably realized.

Second Embodiment

Next, a second embodiment will be described. In the following description, the same reference numerals are given to the same configurations as those of the above-described first embodiment, and a detailed description thereof will be omitted or simplified.

Figure 16:
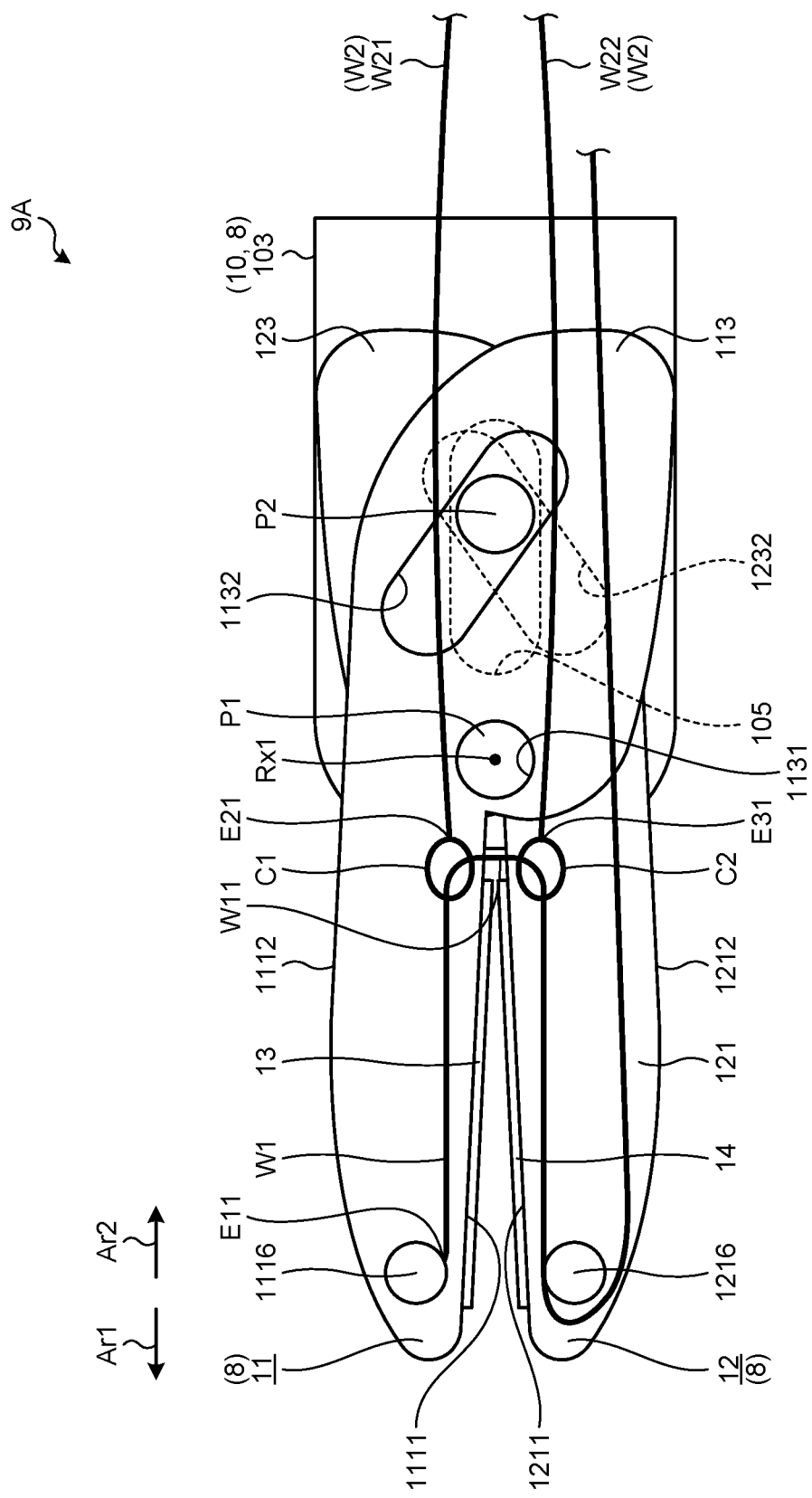
FIG. 16 is a view illustrating a configuration of a gripping device according to a second embodiment.
Figure 17:
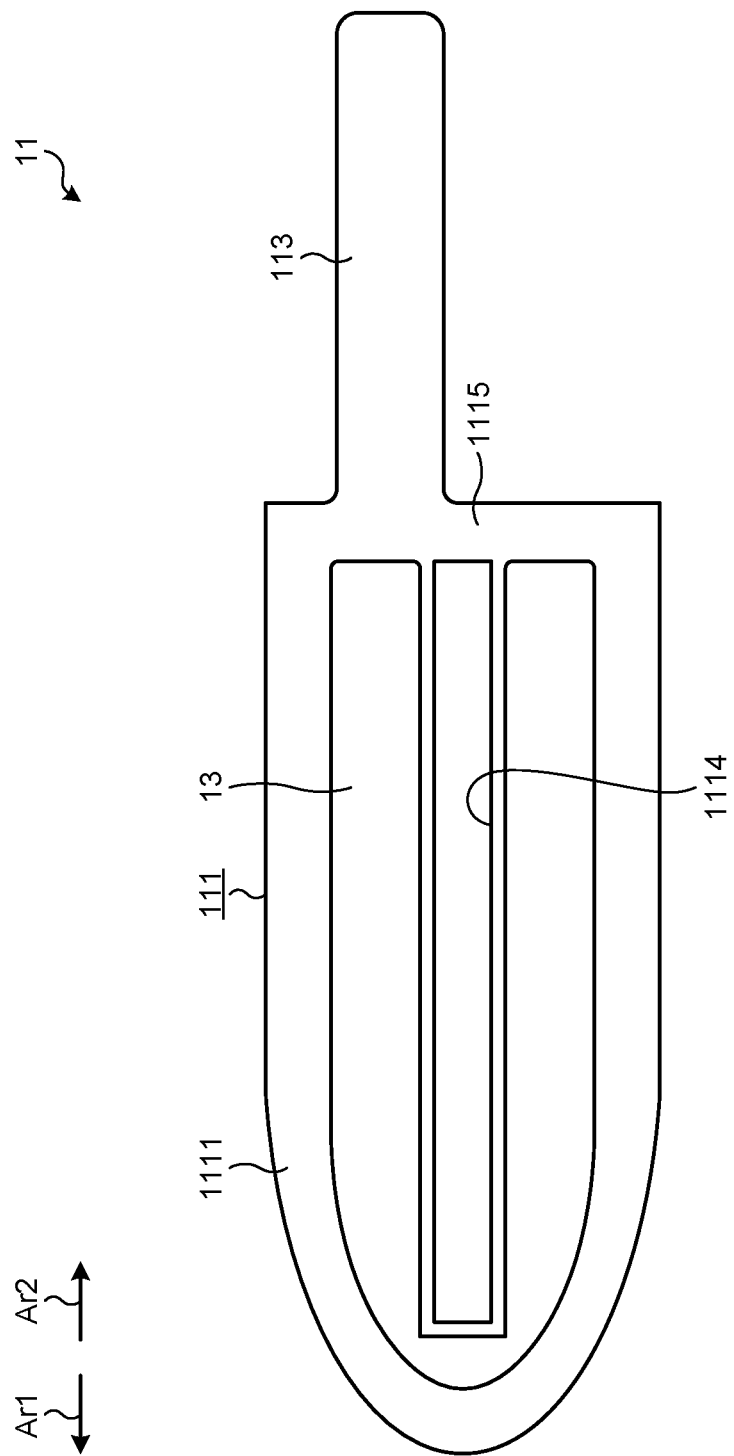
FIG. 17 is a view illustrating a configuration of a first gripping piece according to the second embodiment.
Figure 18:
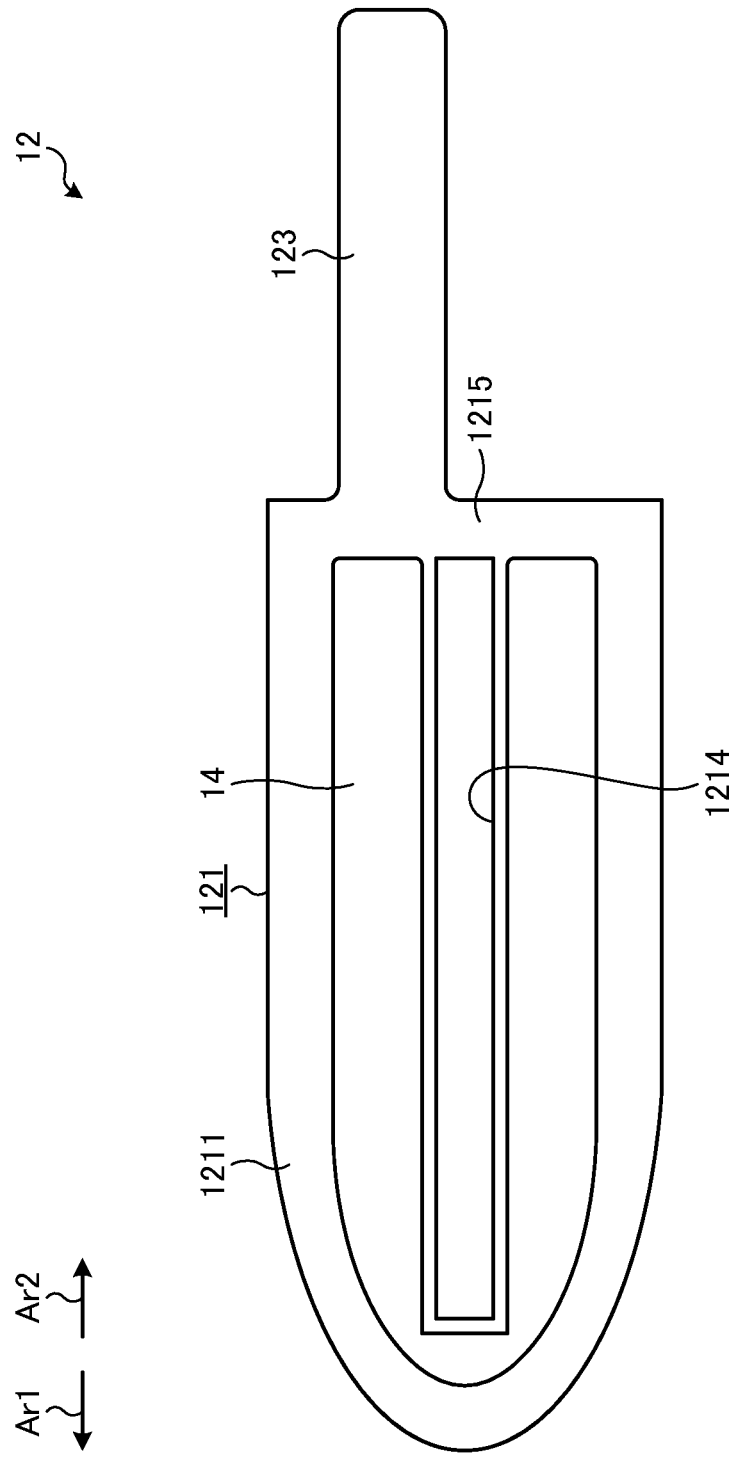
FIG. 18 is a view illustrating a configuration of a second gripping piece according to the second embodiment.

FIG. 16 is a view corresponding to FIG. 11, and is a view illustrating a configuration of a gripping device 9A according to the second embodiment. FIG. 17 is a view corresponding to FIG. 5, and is a view illustrating a configuration of a first gripping piece 11 according to the second embodiment. FIG. 18 is a view corresponding to FIG. 8, and is a view illustrating a configuration of a second gripping piece 12 according to the second embodiment.

In the gripping device 9A according to the second embodiment, as illustrated in FIG. 16, first and second electrodes 13 and 14 are added to the gripping device 9 in the first embodiment described above.

The first electrode 13 corresponds to an electrode. The first electrode 13 is a U-shaped or O-shaped plate body in plan view made of an electrically conductive material such as stainless steel, and is fixed on the first gripping surface 1111 in a posture surrounding the first communication hole 1114 (FIG. 17).

The second electrode 14 corresponds to an electrode. The second electrode 14 is a U-shaped or O-shaped plate body in plan view made of an electrically conductive material such as stainless steel, and is fixed on the second gripping surface 1211 in a posture surrounding the second communication hole 1214 (FIG. 18).

A pair of lead wires (not illustrated) constituting an electric cable (not illustrated) connected to an external control device (not illustrated) is connected to the first and second electrodes 13 and 14. Then, high-frequency power is supplied to the first and second electrodes 13 and 14 via the pair of lead wires under the control of the control device. As a result, a high-frequency current flows through the target site LT held between the first and second electrodes 13 and 14. In other words, high frequency energy is applied from the first and second electrodes 13 and 14 to the target site LT. Then, the target site LT is coagulated.

That is, in the gripping device 9A according to the second embodiment, while the target site LT is coagulated by applying the high frequency energy to the target site LT from the first and second electrodes 13 and 14, the target site LT is incised by the first wire W1.

Although not specifically illustrated, the pair of lead wires connected to the first and second electrodes 13 and 14 are routed from the distal end side Ar1 toward the proximal end side Ar2 inside the base portion 10 and the shaft 7, and then routed inside the housing 2, similarly to the first and second wires W1 and W2. Then, the pair of lead wires routed inside the housing 2 is drawn out to the outside of the housing 2 and connected to the control device described above.

The first and second cover portions 112, 122 according to the second embodiment are made of, for example, a resin material having electrical insulation properties.

According to the above-described second embodiment, in addition to the same effect as the above-described first embodiment, there is an effect that the target site LT can be incised while the target site LT is coagulated.

First Modification of Second Embodiment

Figure 19:
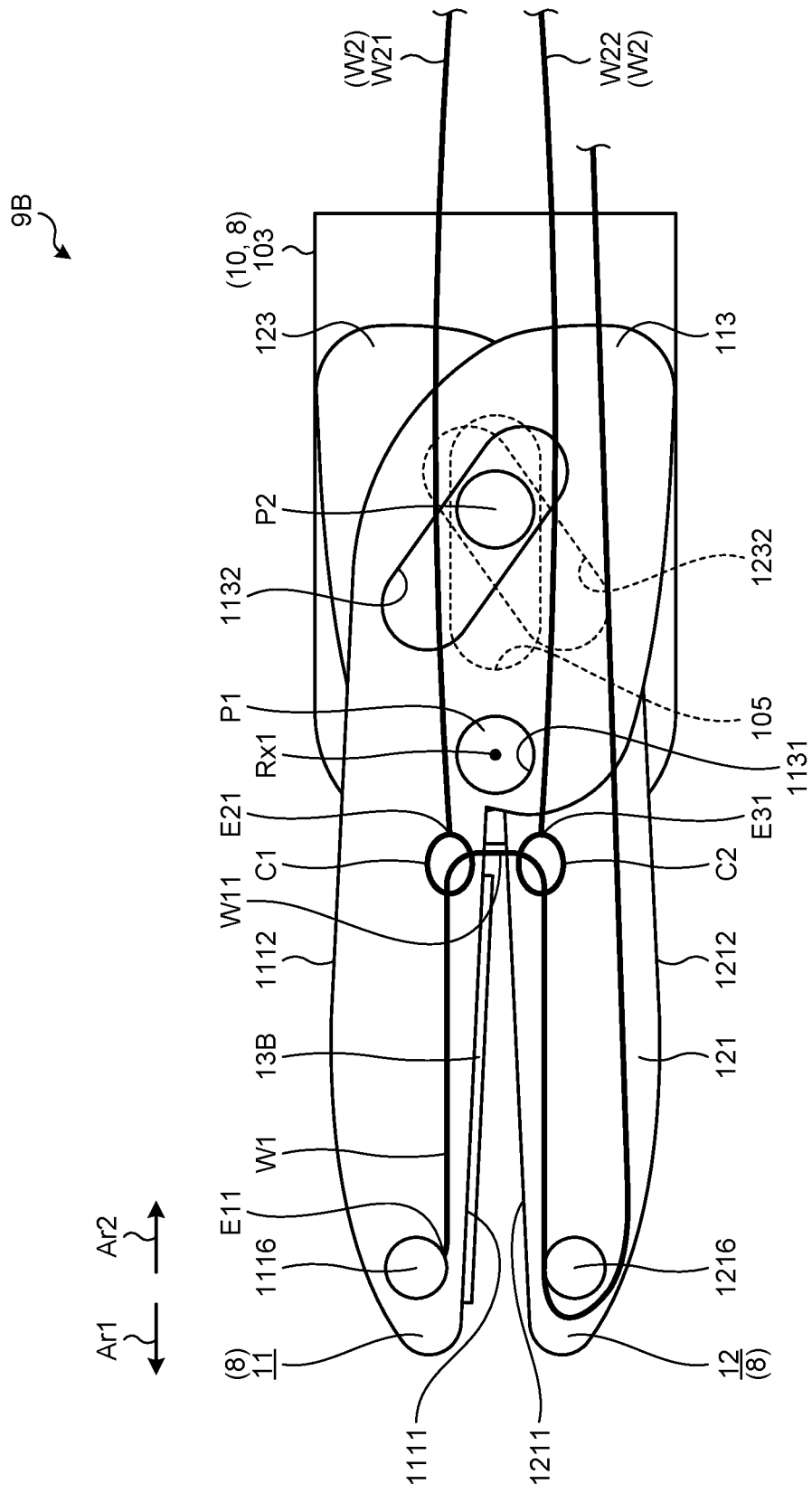
FIG. 19 is a view illustrating a first modification of the second embodiment.
Figure 20:
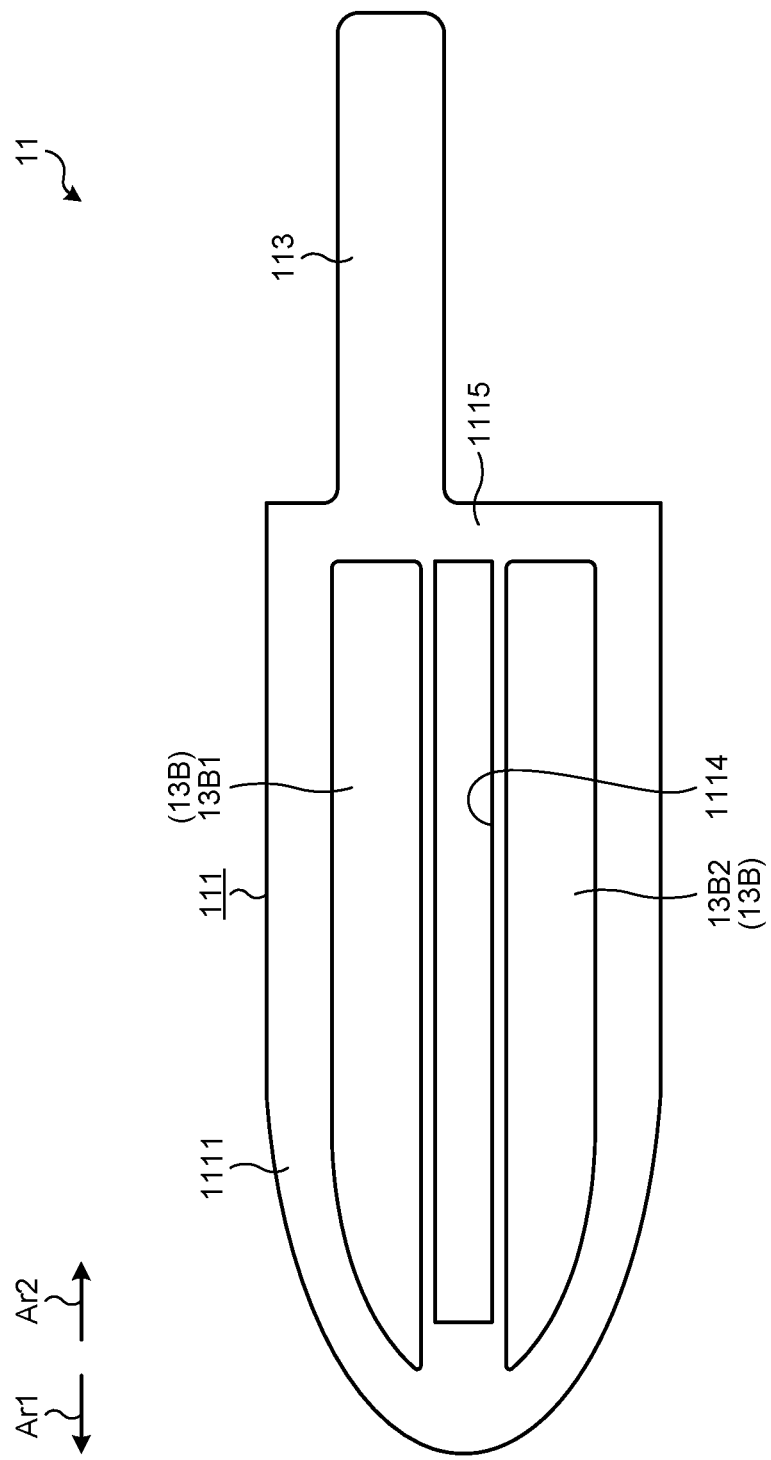
FIG. 20 is a view illustrating the first modification of the second embodiment.

FIGS. 19 and 20 are views illustrating a first modification of the second embodiment. Specifically, FIG. 19 is a view corresponding to FIG. 16, and is a view illustrating a configuration of a gripping device 9B according to the first modification. FIG. 20 is a view corresponding to FIG. 17, and is a view illustrating a configuration of a first gripping piece 11 according to first modification.

In the above-described second embodiment, the electrode is provided on both the first and second gripping pieces 11 and 12, but the disclosure is not limited thereto.

For example, as in the gripping device 9B illustrated in FIGS. 19 and 20, an electrode 13B may be provided only on the first gripping piece 11. As illustrated in FIG. 20, the electrode 13B includes two electrodes 13B1 and 13B2.

As illustrated in FIG. 20, each of the two electrodes 13B1 and 13B2 is a long plate, and is fixed on the first gripping surface 1111 in a posture in which a longitudinal direction of each electrode is along the longitudinal direction of the first gripping piece 11 and the first communication hole 1114 is sandwiched in the width direction (In FIG. 20, the up-down direction).

The pair of lead wires described in the above-described second embodiment is connected to each of the two electrodes 13B1 and 13B2. Then, high-frequency power is supplied to the two electrodes 13B1 and 13B2 via the pair of lead wires under the control of an external control device. As a result, a high-frequency current flows through the target site LT gripped between the first and second gripping pieces 11 and 12. In other words, high-frequency energy is applied to the target site LT from the two electrodes 13B1 and 13B2. Then, the target site LT is coagulated.

According to the above-described first modification, in addition to the effect similar to that of the above-described second embodiment, the position (in FIG. 19, the upper side) at which the pair of lead wires are routed and the position (in FIG. 19, lower side) at which the first wire W1 is routed can be set to different positions. That is, the size of the gripping device 9B (distal end portion of the treatment tool 1) can be reduced as compared with a configuration in which the position at which the lead wire is routed and the position at which the first wire W1 is routed are at the same position.

Third Embodiment

Next, a third embodiment will be described.

In the following description, the same reference numerals are given to the same configurations as those of the above-described first embodiment, and a detailed description thereof will be omitted or simplified.

Figure 21:
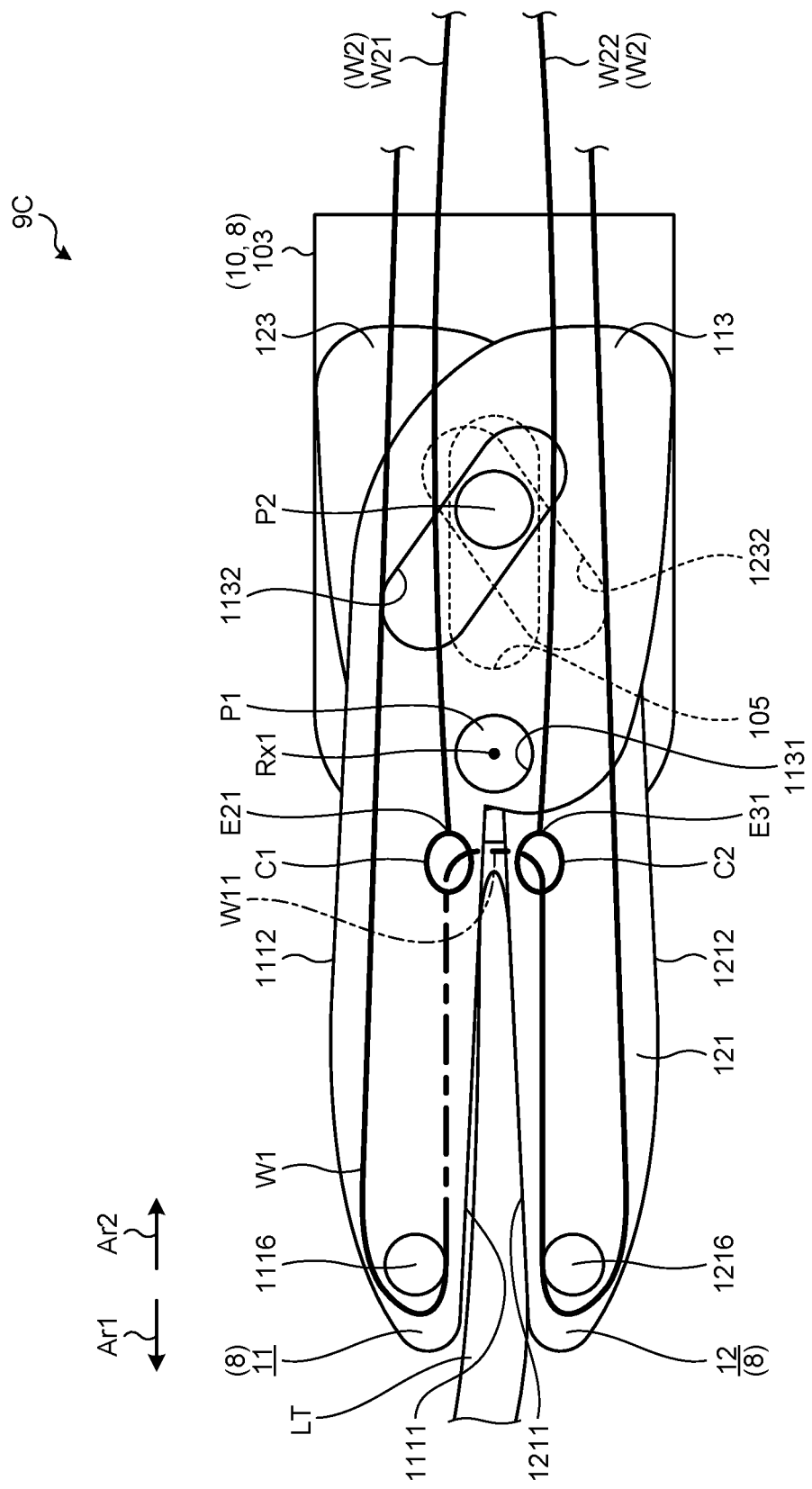
FIG. 21 is a view illustrating a configuration of a gripping device according to a third embodiment.
Figure 22:
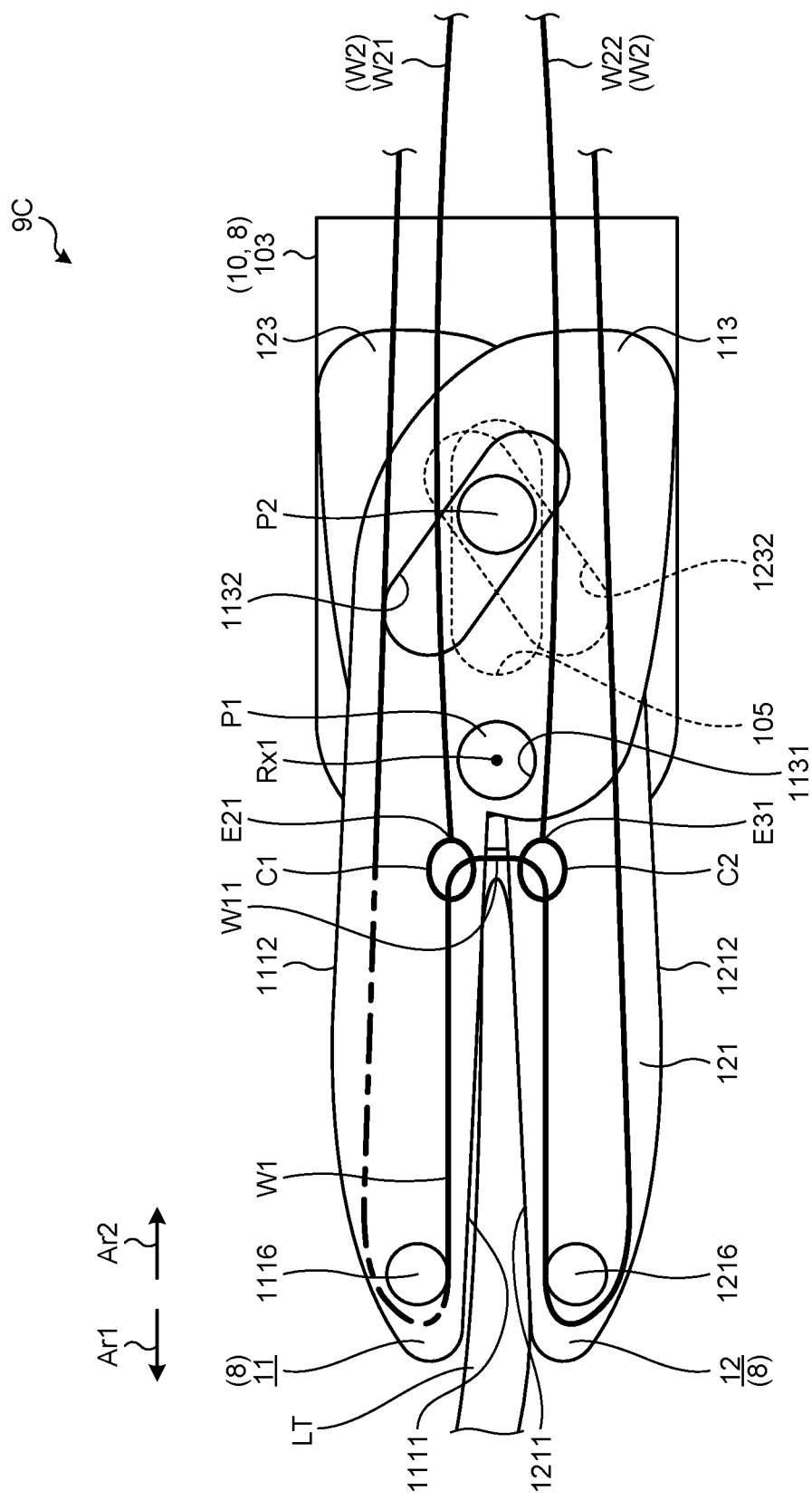
FIG. 22 is a view illustrating a configuration of the gripping device according to the third embodiment.

FIGS. 21 and 22 are views corresponding to FIG. 11, and are views illustrating a configuration of a gripping device 9C according to the third embodiment.

As illustrated in FIG. 21 or 22, the gripping device 9C according to the third embodiment is different from the gripping device 9 described in the first embodiment in the method of routing the first wire W1 inside the gripping portion 8.

As illustrated in FIG. 21 or 22, the first end E11 of the first wire W1 according to the third embodiment is not fixed to the fixed shaft portion 1116. More specifically, the portion of the first wire W1 on the first end E11 side is routed toward the distal end side Ar1 inside the first accommodation hole 1113, then folded back at the fixed shaft portion 1116, and again routed toward the proximal end side Ar2. The portion of the first wire W1 on the second end E12 side is similar to that of the first embodiment described above. That is, the first wire W1 is routed toward the proximal end side Ar2 in a state where a portion between the first end E11 and the second end E12 is hooked to the fixed shaft portion 1116 and the support shaft 1216.

That is, the fixed shaft portion 1116 corresponds to a first support shaft. The support shaft 1216 corresponds to a second support shaft.

The first and second wires W1 and W2 operate as follows. Note that the operations of the first and second wires W1 and W2 may be manually operated in accordance with the operation of the handle by the operator as in the above-described first embodiment, or may be electrically operated in accordance with the drive of a motor or the like by the operator pressing a switch.

In the first wire W1, the first end E11 is alternately pulled toward the proximal end side Ar2 and pushed toward the distal end side Ar1. Meanwhile, the second end E12 is alternately pushed toward the distal end side Ar1 and pulled toward the proximal end side Ar2 contrary to the first end E11. As a result, the incision portion W11 moves forward and backward in the up-down direction in FIGS. 21 and 22 (hereinafter, described as a first operation).

In addition, when the first operation is performed, the first end E11 and the second end E12 are pulled toward the proximal end side Ar2. As a result, the incision portion W11 moves from the first position illustrated in FIGS. 21 and 22 toward the distal end side Ar1 (hereinafter, described as a second operation). Then, the target site LT is incised by the incision portion W11 by the first and second operations in the above-described first wire W1, similarly to the incision by the saw. In addition, after the incision of the target site LT, the second wire W2 operates in the same manner as in the above-described first embodiment, and returns the incision portion W11 to the first position illustrated in FIGS. 21 and 22.

According to the above-described third embodiment, the following effects are obtained in addition to the same effects as those of the first embodiment described above.

In the gripping device 9C according to the third embodiment, both the first end E11 and the second end E12 of the first wire W1 are not fixed to the gripping portion 8. Therefore, after the incision of the target site LT is performed, for example, by pulling the first end E11, it is possible to adopt a configuration in which the portion used for the incision (the alternate long and short dash line in FIGS. 21 and 22) is not used in the next incision.

In addition, by the first wire W1 moving in a saw shape, the force for incision can be reduced.

Fourth Embodiment

Next, a fourth embodiment will be described.

In the following description, the same reference numerals are given to the same configurations as those of the above-described first embodiment, and a detailed description thereof will be omitted or simplified.

Figure 23:
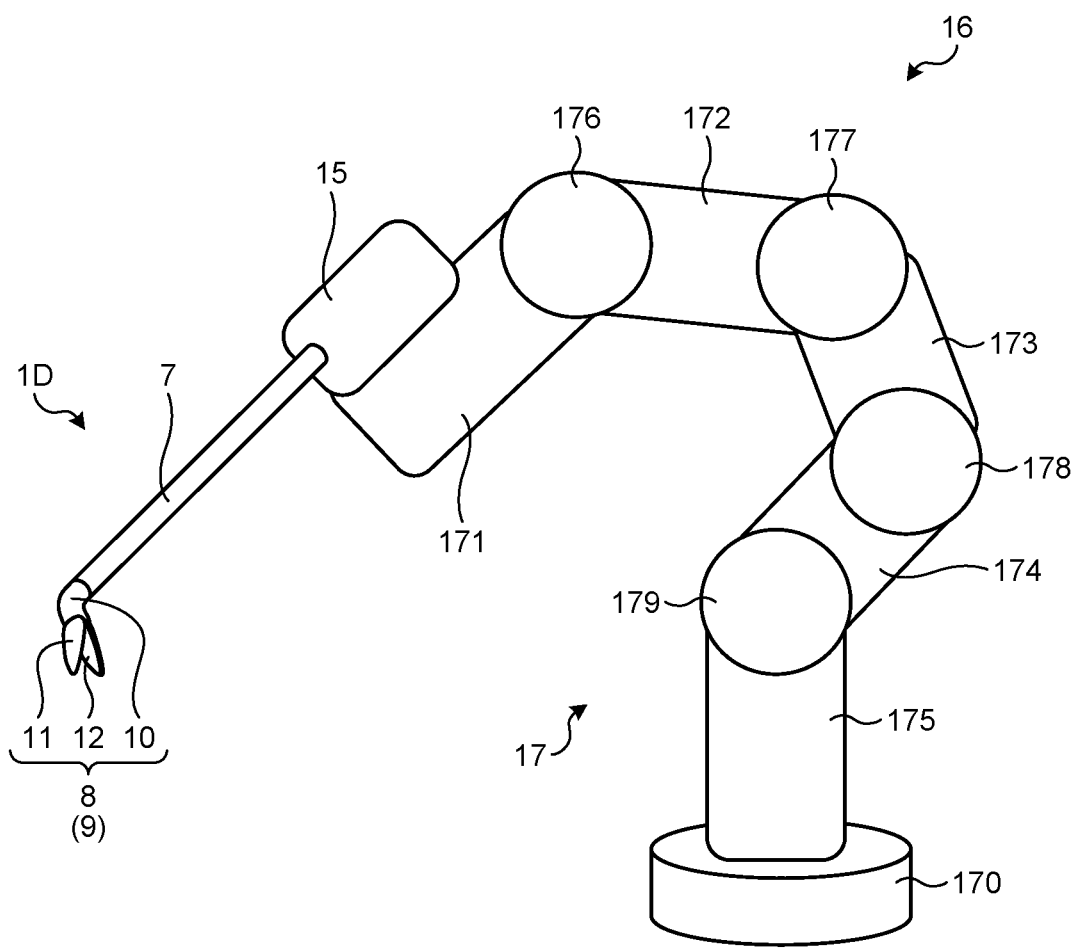
FIG. 23 is a view illustrating a configuration of a medical device according to a fourth embodiment.
Figure 24:
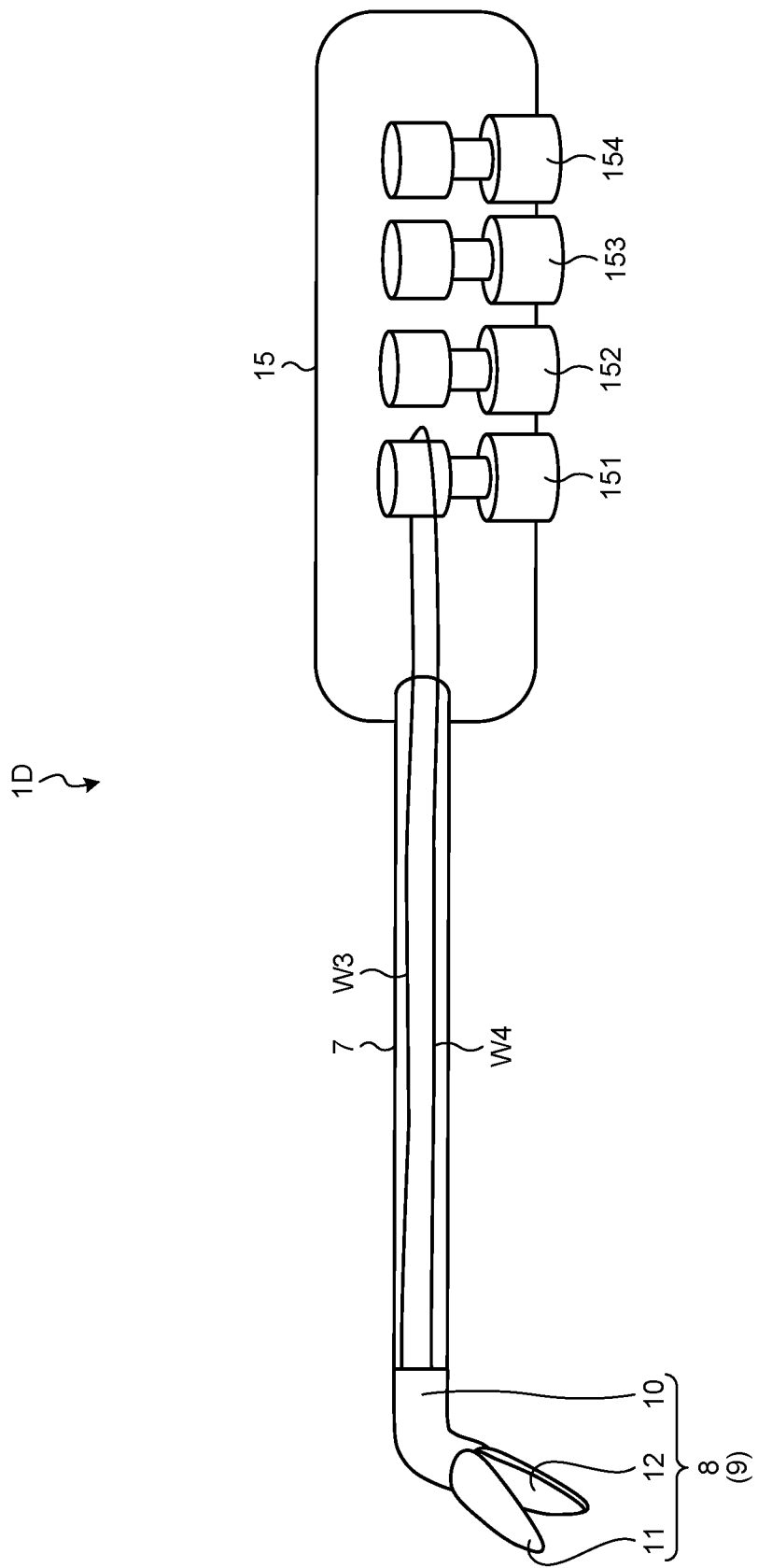
FIG. 24 is a view illustrating a configuration of a treatment tool according to the fourth embodiment.

FIG. 23 is a view illustrating a configuration of a medical device 16 according to the fourth embodiment. FIG. 24 is a view illustrating a configuration of a treatment tool 1D according to the fourth embodiment.

As illustrated in FIG. 23 or 24, the medical device 16 according to the fourth embodiment has a configuration in which the treatment tool 1D having a configuration different from that of the treatment tool 1 of the first embodiment described above is supported by a robot arm 17 (FIG. 23).

As illustrated in FIG. 23, the robot arm 17 includes a base portion 170, first to fifth arm portions 171 to 175, and first to fourth joint portions 176 to 179.

The base portion 170 is installed on a floor surface or the like, and supports the entire robot arm 17.

The first to fifth arm portions 171 to 175 are connected in series by first to fourth joint portions 176 to 179. Among the first to fifth arm portions 171 to 175, the fifth arm portion 175 located at the proximal end is fixed on the base portion 170. In addition, the treatment tool 1D is detachably connected to the first arm portion 171 located at the distal end among the first to fifth arm portions 171 to 175.

The first to fourth joint portions 176 to 179 relatively rotate a pair of mutually connected arm portions in the first to fifth arm portions 171 to 175 about mutually different axes. That is, in the fourth embodiment, the treatment tool 1D is movable in four degrees of freedom. Note that the robot arm 17 is not limited to four degrees of freedom, and may have another different number of degrees of freedom. That is, the number of the first to fifth arm portions 171 to 175 and the number of the first to fourth joint portions 176 to 179 are not limited to the above-described numbers, and may be other numbers.

Although not specifically illustrated, actuators for relatively rotating a pair of mutually connected arm portions in the first to fifth arm portions 171 to 175 are provided inside the first to fourth joint portions 176 to 179. Each actuator is driven under the control of an external control device (not illustrated).

As illustrated in FIG. 23 or 24, the treatment tool 1D includes a detachable portion 15 in addition to the shaft 7 and the gripping device 9 described in the first embodiment described above.

The detachable portion 15 is a part that is provided at the proximal end of the shaft 7 and attaches and detaches the treatment tool 1D to and from the robot arm 17 (first arm portion 171). As illustrated in FIG. 24, power transmission portions 151 to 154 such as a pulley are provided inside the detachable portion 15.

The power transmission portions 151 to 154 are parts that transmit power by a motor provided in the robot arm 17 in a state where the detachable portion 15 is connected to the robot arm 17. The power transmission portions 151 to 154 constitute a part of an opening/closing mechanism for opening and closing the first and second gripping pieces 11 and 12, a part of a bending mechanism for bending the gripping portion 8, and a part of an incision mechanism for operating the first and second wires W1 and W2. That is, the opening/closing operation of the first and second gripping pieces 11 and 12, the bending operation of the gripping portion 8, and the operation of the first and second wires W1 and W2 are performed by driving the motor under the control of the control device described above.

Note that the above-described motor is not limited to the configuration provided in the robot arm 17, and may be provided in the treatment tool 1D.

According to the above-described fourth embodiment, effects similar to those of the first embodiment described above are obtained.

Other Embodiments

Although the embodiments for carrying out the disclosure have been described so far, the disclosure should not be limited only by the above-described first to fourth embodiments and the first modification.

Figure 25:
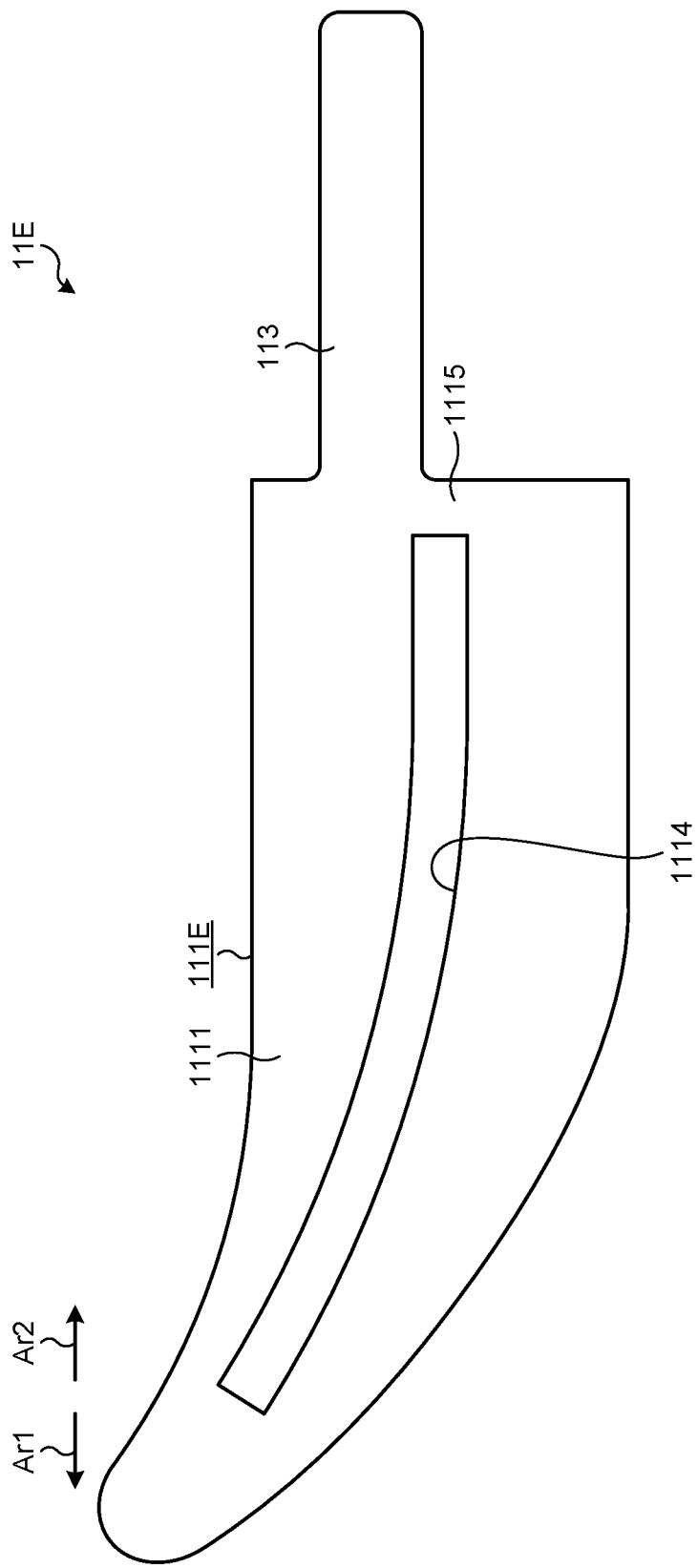
FIG. 25 is a view illustrating a second modification of the first to fourth embodiments.
Figure 26:
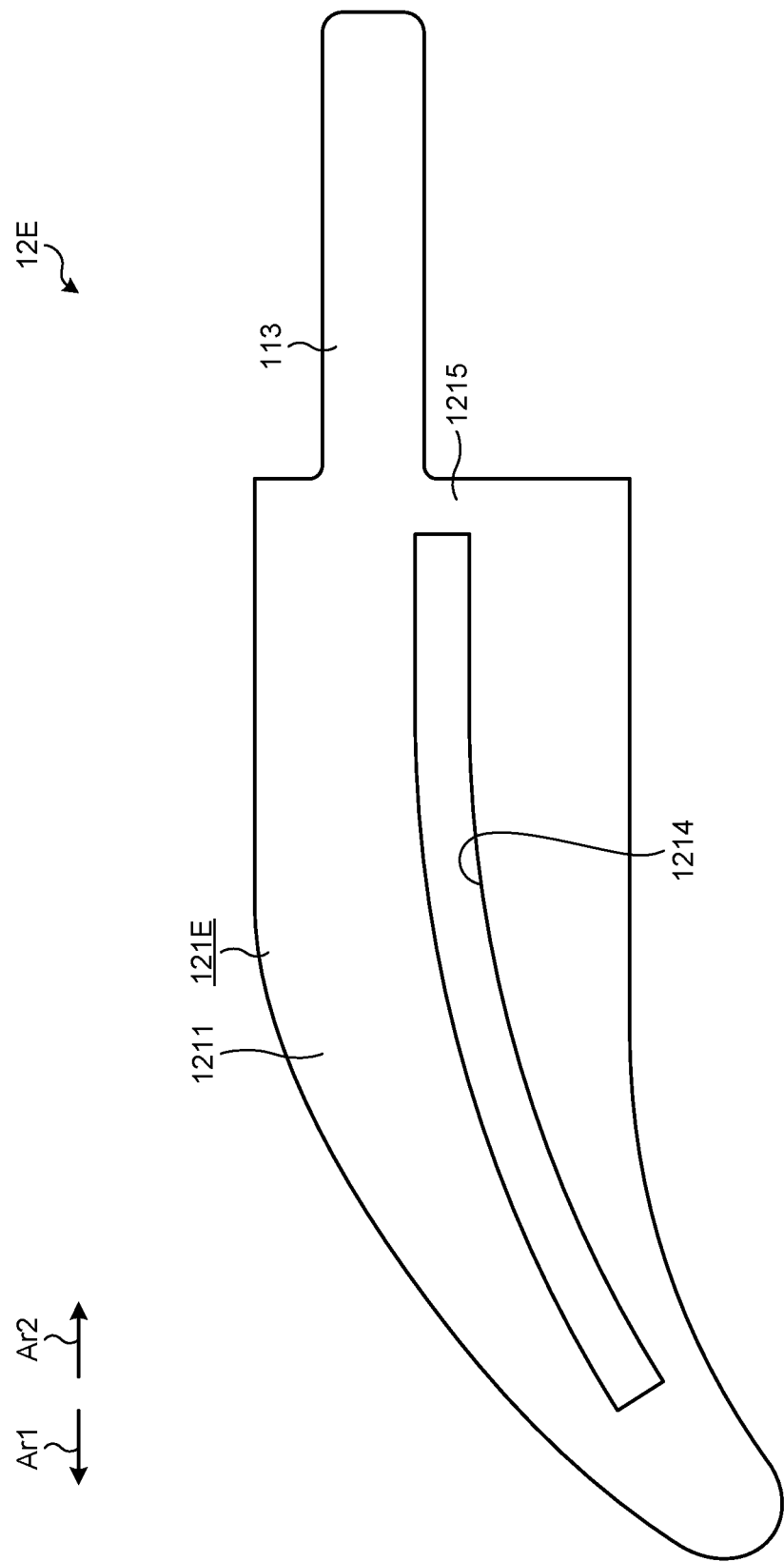
FIG. 26 is a view illustrating the second modification of the first to fourth embodiment.

FIGS. 25 and 26 are views illustrating a second modification of the first to fourth embodiments. Specifically, FIG. 25 is a view corresponding to FIG. 5, and is a view illustrating a configuration of a first gripping piece 11E according to the second modification. FIG. 26 is a view corresponding to FIG. 8, and is a view illustrating a configuration of a second gripping piece 12E according to the second modification.

In the above-described first to fourth embodiments and first modification, the first and second gripping pieces 11E and 12E according to the second modification may be adopted.

In the first gripping piece 11E, as illustrated in FIG. 25, a first gripping piece body 111E having a shape different from that of the first gripping piece body 111 is adopted with respect to the first gripping piece 11 of the above-described first to fourth embodiments and the first modification.

The first gripping piece body 111E has a shape that is curved upward and tapered in FIG. 25 toward the distal end side Ar1. The first communication hole 1114 is also curved in accordance with the curve of the first gripping piece body 111E. Although not specifically illustrated, the first accommodation hole 1113 is similarly curved.

In the second gripping piece 12E, as illustrated in FIG. 26, a second gripping piece body 121E having a shape different from that of the second gripping piece body 121 is adopted with respect to the second gripping piece 12 of the above-described first to fourth embodiments and the first modification.

The second gripping piece body 121E corresponds to the first gripping piece body 111E and has a shape that is curved downward and tapered in FIG. 26 toward the distal end side Ar1. The second communication hole 1214 is also curved in accordance with the curve of the second gripping piece body 121E. Although not specifically illustrated, the second accommodation hole 1213 is similarly curved.

In the above-described first to fourth embodiments and first and second modifications, two second wires W2 such as the second wires W21 and W22 are provided, but the disclosure is not limited thereto, and one or three or more second wires W2 may be provided. Further, a configuration in which the second wire W2 is not provided, that is, a configuration in which incision is performed only once may be adopted.

In the above-described first to fourth embodiments and the first and second modifications, the second wire W2 is connected to the first wire W1 so as to be relatively movable by the first and second connection portions C1 and C2. However, the disclosure is not limited thereto, and the second wire W2 may be fixed to the first wire W1 so as not to be movable.

In the above-described first to fourth embodiments and first and second modifications, the first and second positioning portions 1115 and 1215 are provided in the first and second gripping pieces 11 (11E) and 12 (12E), but the disclosure is not limited thereto. A part having the same function as the first and second positioning portions 1115 and 1215 may be provided in another part (for example, the first and second attachment portions 113,123 and the like). Note that the first and second positioning portions 1115 and 1215 function to "pull the first wire W1 to cause the first and second connection portions C1 and C2 to always enter the first and second accommodation holes 1113 and 1213 from the proximal ends of the first and second gripping piece bodies 111 and 121 when the first and second connection portions C1 and C2 come out of the first and second accommodation holes 1113 and 1213 from the proximal ends of the first and second gripping piece bodies 111 and 121".

In the above-described first to fourth embodiments and first and second modifications, when the first and second wires W1 and W2 are routed inside the base portion 10 and the shaft 7, the first and second wires W1 and W2 may be routed, for example, one by one in a state of being inserted into a shaft different from the shaft 7.

In the above-described first to fourth embodiments and first and second modifications, the joint for bending the gripping portion 8 is not limited to one degree of freedom, and may be two or more degrees of freedom.

In the above-described first and third embodiments, the first wire W1 is made of a resin material, but the disclosure is not limited thereto. For example, the first wire W1 may be made of an electrically conductive material. Then, high-frequency power is supplied between the first wire W1 and a counter electrode plate attached to the surface of a subject under the control of an external control device. As a result, a high-frequency current flows through the target site LT gripped between the first and second gripping surfaces 1111 and 1211. That is, the target site LT is incised by the first wire W1 while coagulating.

In the above-described second embodiment and the first modification, the first wire W1 is made of a resin material, but the disclosure is not limited thereto. For example, the first wire W1 may be made of an electrically conductive material. Then, high-frequency power is supplied between the first wire W1 and the first electrode 13 (electrode 13B) or the second electrode 14 under the control of an external control device. As a result, a high-frequency current flows through the target site LT held between the first and second electrodes 13 and 14. That is, the target site LT is incised by the first wire W1 while coagulating.

In the above-described second embodiment and the first modification, the high frequency energy is exemplified as the treatment energy applied to the target site LT, but the treatment energy is not limited thereto, and thermal energy, ultrasonic energy, or the like may be adopted. Here, "applying thermal energy to the target site LT" means that heat of a heater or the like is transferred to the target site LT. In addition, "applying ultrasonic energy to the target site LT" means applying ultrasonic vibration to the target site LT.

According to the gripping device and the treatment tool according to the disclosure, a size of the gripping device can be reduced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A gripping device comprising:
a gripping portion including
a first gripping piece including a first gripping surface, and
a second gripping piece including a second gripping surface that is relatively opened or closed with respect to the first gripping piece, the second gripping surface being configured to grip a living tissue between the second gripping surface and the first gripping surface; and
a first wire extending from a first end to a second end of the first wire, an incision portion that is a part of the first wire between the first end and the second end being bridged between the first gripping surface and the second gripping surface,
the first wire being configured such that the incision portion moves from a first position toward a distal end of the gripping portion according to pulling of at least one of the first end and the second end to incise the living tissue gripped between the first gripping surface and the second gripping surface.

2. The gripping device according to claim 1,
wherein a support shaft which extends in a direction intersecting a longitudinal direction connecting a distal end and a proximal end of the second gripping piece and to which the first wire is hooked is provided at a distal end portion of the second gripping piece, and
the first wire is routed toward a proximal end of the second gripping piece in a state in which the first end is fixed to a distal end portion of the first gripping piece and a portion of the first wire between the first end and the second end is hooked to the support shaft.

3. The gripping device according to claim 1,
wherein a first support shaft which extends in a direction intersecting a longitudinal direction connecting a distal end and a proximal end of the first gripping piece and to which the first wire is hooked is provided at a distal end portion of the first gripping piece,
a second support shaft which extends in a direction intersecting a longitudinal direction connecting a distal end and a proximal end of the second gripping piece and to which the first wire is hooked is provided at a distal end portion of the second gripping piece,
the first wire is routed toward a proximal end of the first gripping piece in a state in which a portion of the first wire between the first end and the second end is hooked to the first support shaft, and
the first wire is routed toward a proximal end of the second gripping piece in a state in which a portion of the first wire between the first end and the second end is hooked to the second support shaft.

4. The gripping device according to claim 1, further comprising
a second wire including a connector connected to the first wire, the second wire being configured to move the incision portion toward the first position by being pulled.

5. The gripping device according to claim 4,
wherein the connector is connected to the first wire so as to be relatively movable.

6. The gripping device according to claim 5,
wherein the second wire is one of two second wires,
the first gripping piece includes
a first accommodation hole extending along a first longitudinal direction connecting a distal end and a proximal end of the first gripping piece, and
a first communication hole extending along the first longitudinal direction and allowing the first accommodation hole to communicate with an outside of the first gripping piece through the first gripping surface,
the second gripping piece includes
a second accommodation hole extending along a second longitudinal direction connecting a distal end and a proximal end of the second gripping piece, and
a second communication hole extending along the second longitudinal direction and allowing the second accommodation hole to communicate with an outside of the second gripping piece through the second gripping surface,
connectors of the two second wires are accommodated in the first accommodation hole and the second accommodation hole, and
a width dimension of each of the first communication hole and the second communication hole is smaller than a size of the connector.

7. The gripping device according to claim 4,
wherein the connector is formed in a ring shape, and the first wire is inserted through the connector.

8. The gripping device according to claim 1,
wherein an electrode is provided at least one of the first gripping surface and the second gripping surface.

9. The gripping device according to claim 1,
wherein the first wire is made of an electrically conductive material.

10. The gripping device according to claim 9,
wherein an electrode is provided at least one of the first gripping surface and the second gripping surface, and
high frequency power is supplied between the first wire and the electrode.

11. The gripping device according to claim 1,
wherein the first wire is made of a resin material.

12. A treatment tool comprising
a gripping device configured to grip a living tissue, the gripping device including
a gripping portion including
a first gripping piece including a first gripping surface, and
a second gripping piece including a second gripping surface that is relatively opened or closed with respect to the first gripping piece, the second gripping surface being configured to grip a living tissue between the second gripping surface and the first gripping surface; and
a first wire extending from a first end to a second end of the first wire, an incision portion that is a part of the first wire between the first end and the second end being bridged between the first gripping surface and the second gripping surface, the first wire being configured such that the incision portion moves from a first position toward a distal end of the gripping portion according to pulling of at least one of the first end and the second end to incise the living tissue gripped between the first gripping surface and the second gripping surface.

\* \* \* \* \*